United States Patent
Suga et al.

(10) Patent No.: US 7,882,754 B2
(45) Date of Patent: Feb. 8, 2011

(54) GAS COMPONENT COLLECTOR, GAS COMPONENT COLLECTING DEVICE, FILTER PRODUCING METHOD, AND GAS COMPONENT ANALYZING APPARATUS

(75) Inventors: Masao Suga, Hachioji (JP); Masuyoshi Yamada, Ichikawa (JP); Izumi Waki, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 617 days.

(21) Appl. No.: 11/907,905

(22) Filed: Oct. 18, 2007

(65) Prior Publication Data
US 2008/0092629 A1 Apr. 24, 2008

(51) Int. Cl.
G01N 1/22 (2006.01)
(52) U.S. Cl. .................................. 73/863.21
(58) Field of Classification Search ............... None
See application file for complete search history.

(56) References Cited

U.S. PATENT DOCUMENTS

| | | | |
|---|---|---|---|
| 2,686,572 A * | 8/1954 | Cameron et. al. | 96/149 |
| RE38,797 E * | 9/2005 | Linker et al. | 73/863.12 |
| 7,104,112 B2 * | 9/2006 | Bonne | 73/23.25 |
| 7,262,048 B2 * | 8/2007 | Nakajima et al. | 435/287.1 |
| 2004/0191129 A1 * | 9/2004 | Kuruma et al. | 422/101 |
| 2005/0042866 A1 * | 2/2005 | Klapproth et al. | 438/684 |
| 2005/0130222 A1 * | 6/2005 | Lee | 435/7.1 |
| 2006/0266353 A1 | 11/2006 | Yamada et al. | |
| 2006/0266941 A1 * | 11/2006 | Vestal | 250/288 |
| 2007/0062255 A1 * | 3/2007 | Talton | 73/23.3 |

FOREIGN PATENT DOCUMENTS

| | | |
|---|---|---|
| JP | 09-210875 | 2/1996 |
| JP | 2002-328077 | 5/2001 |

* cited by examiner

*Primary Examiner*—Robert R Raevis
(74) *Attorney, Agent, or Firm*—Stites & Harbison, PLLC; Juan Carlos A. Marquez, Esq.

(57) ABSTRACT

A gas component collector comprises a filter assembly 3 comprising an adsorbent and an adsorbent holding plate having a first face, a second face and a plurality of holes that are bored through from the first face to the second face and are filled with the adsorbent adsorbing at least one gas component to be analyzed, the filter assembly satisfying $(AL-V)^2/L^3 \geq 0.003$ mm$^3$ and $V/AL \geq 0.3$, where V is a total volume of the adsorbent, A is a sum of an opening areas of the holes, and L is an average length of the holes, and a holding container 2 housing the filter assembly 3. On at least one of the holding container 2 a first opening portion for introducing gas and a second opening portion for allowing the introduced gas to be discharged are formed.

18 Claims, 16 Drawing Sheets

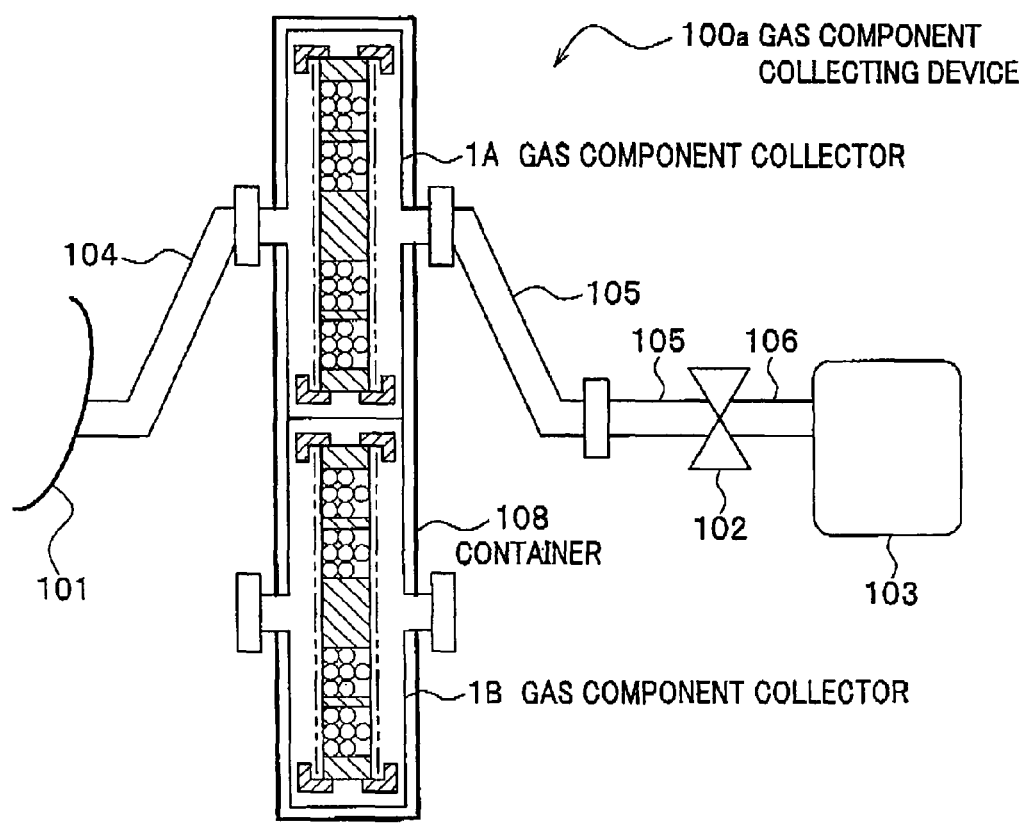

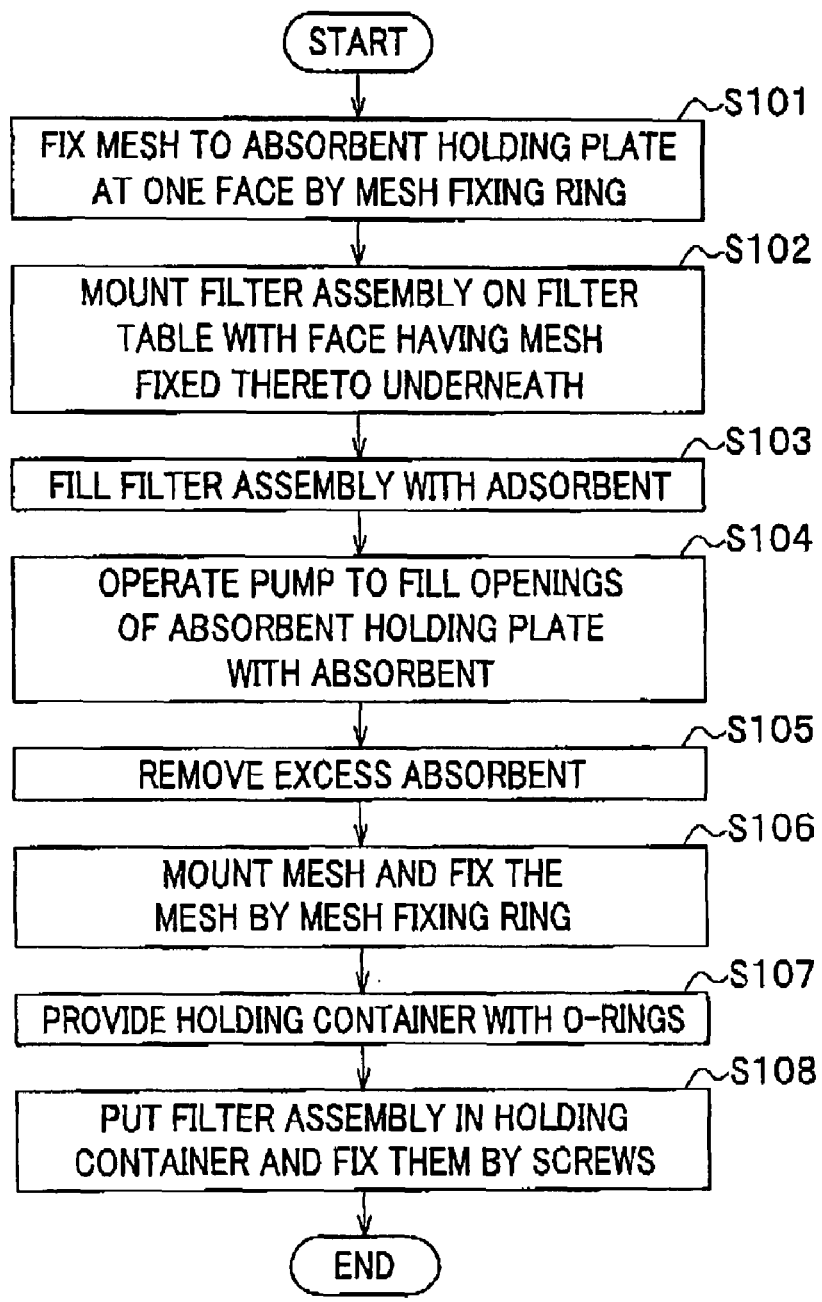

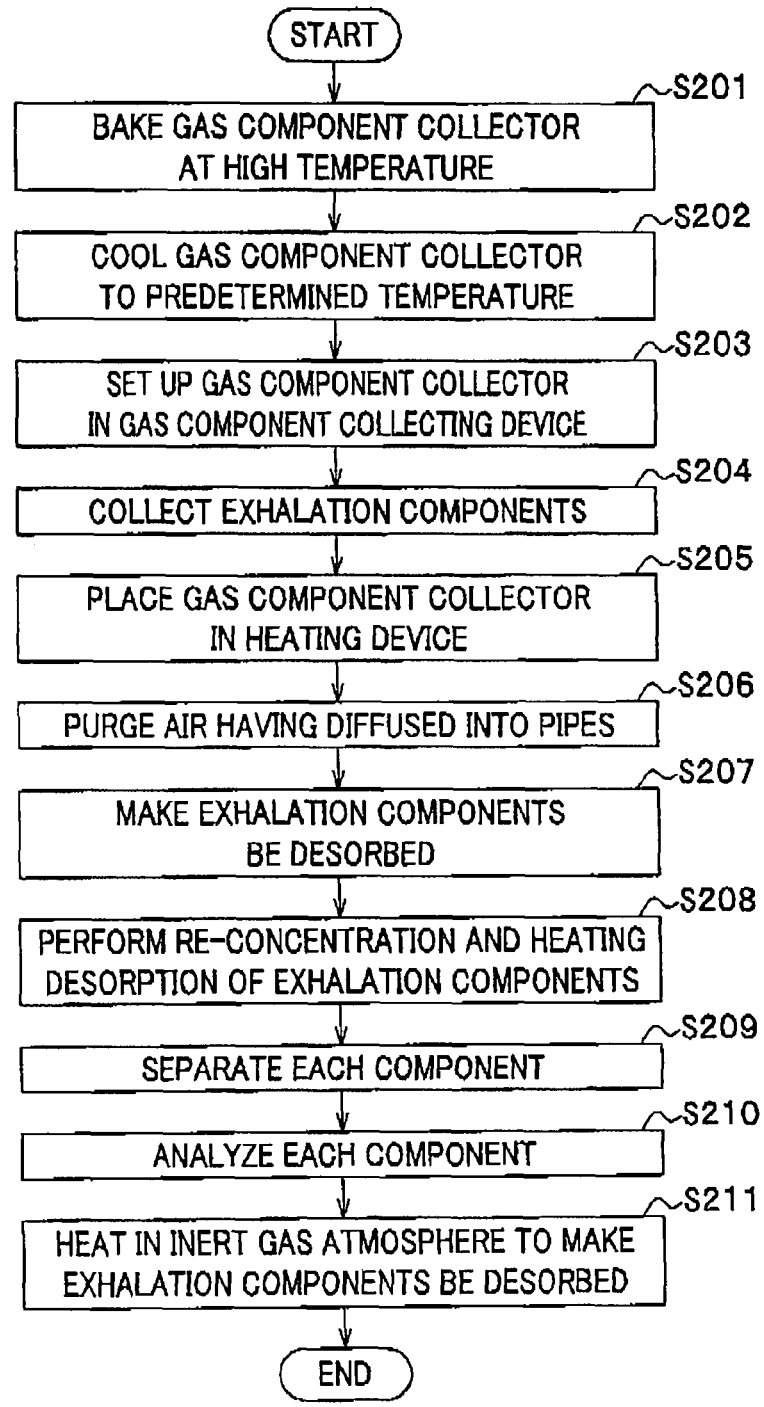

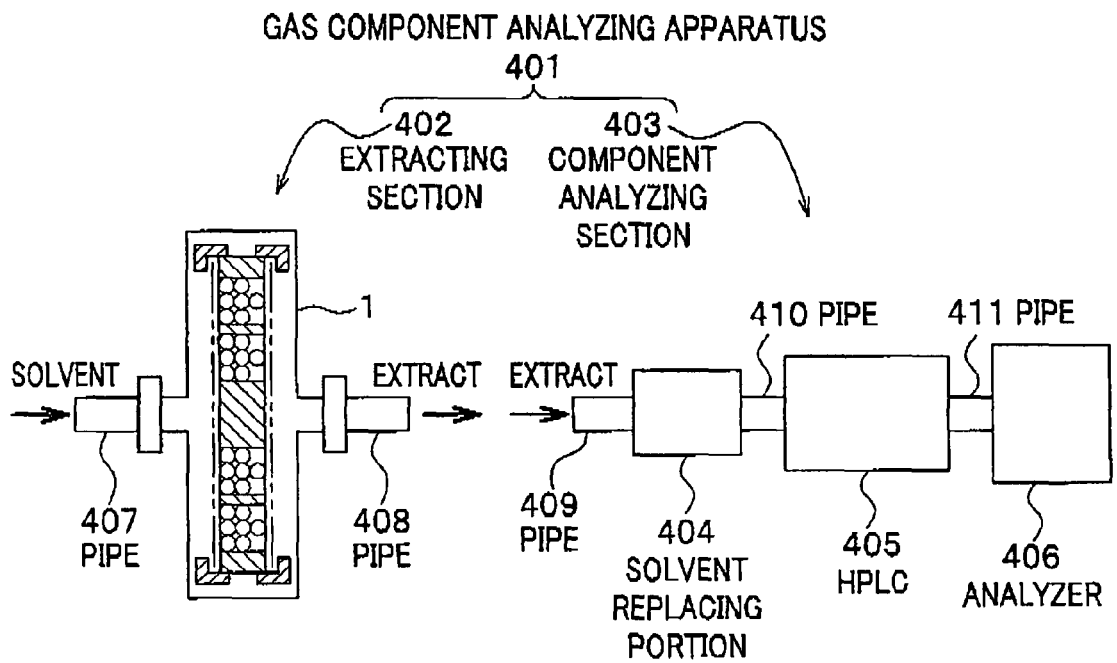
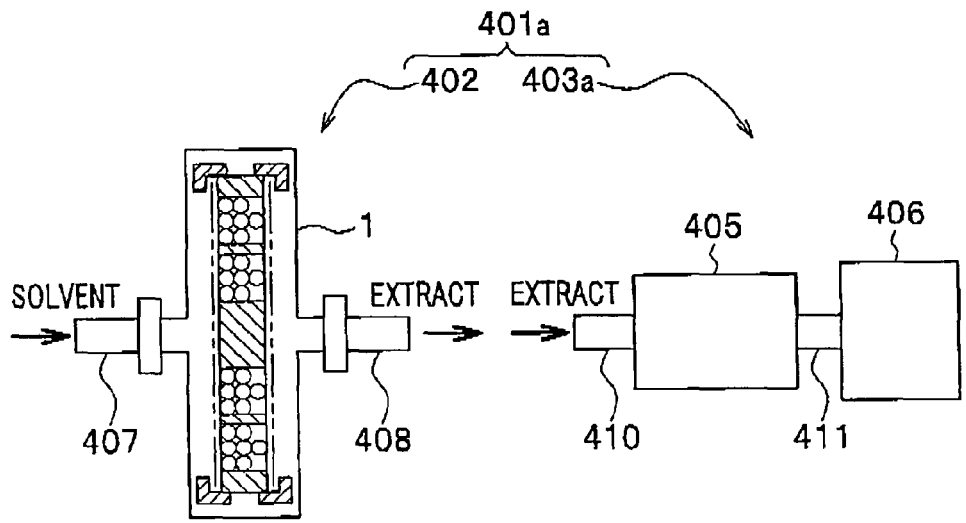

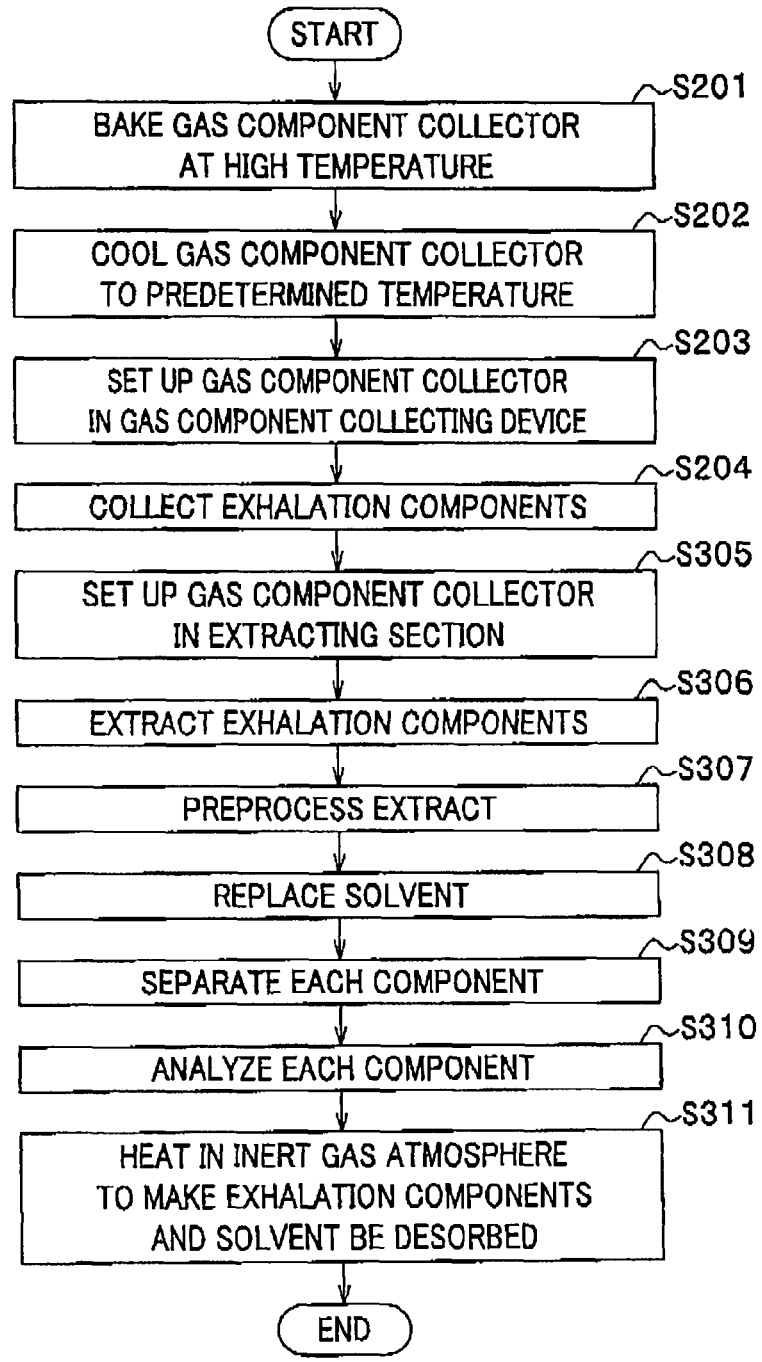

FIG.20A
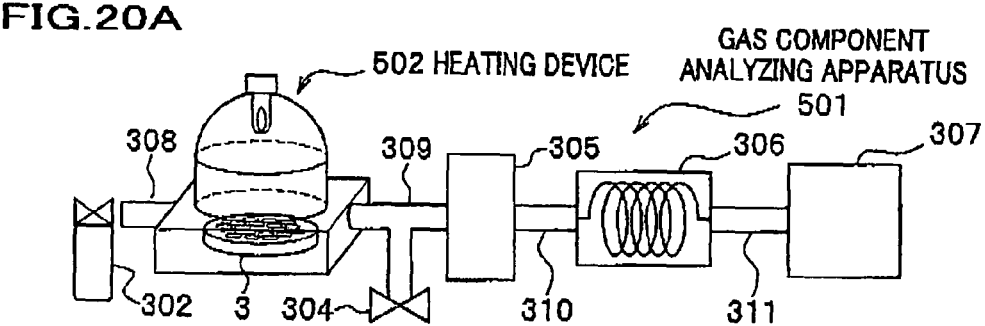
FIG.20B MASS CHROMATOGRAPH OF FRAGMENT IONS OF ACETONE
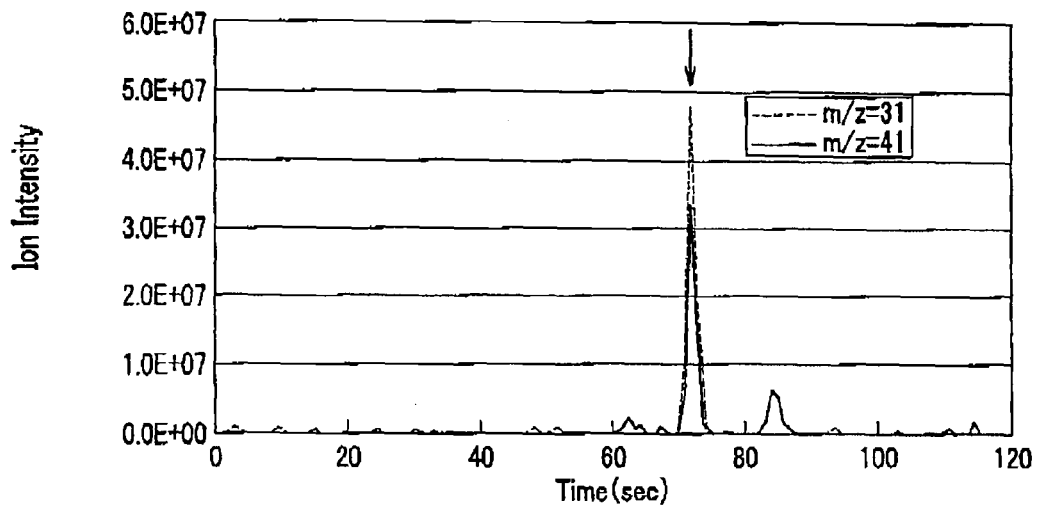
FIG.20C SPECTRUM OF FRAGMENT IONS OF ACETONE
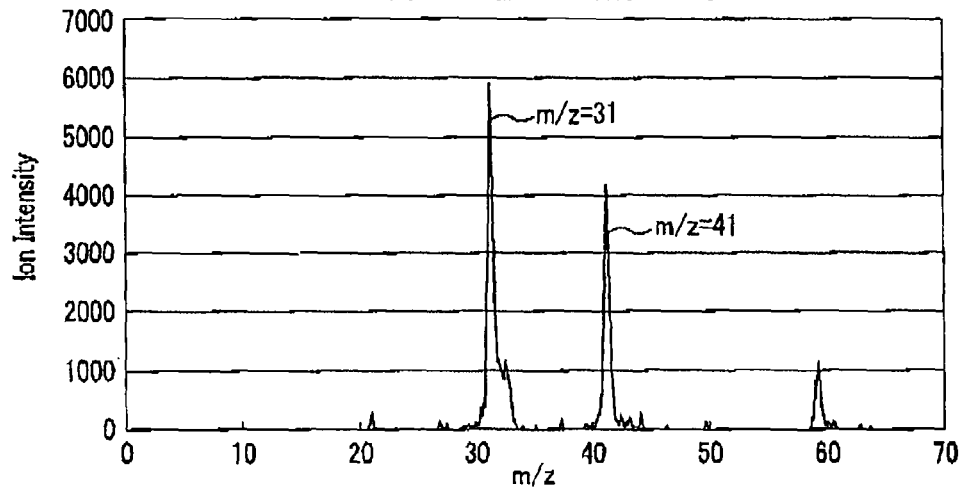

FIG.21A
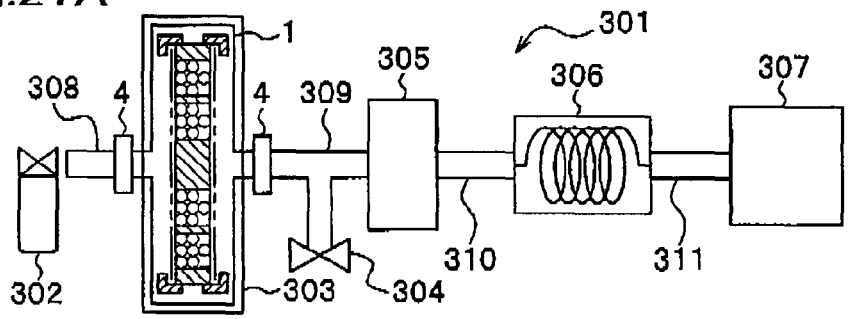
FIG.21B    MASS CHROMATOGRAPH OF FRAGMENT IONS OF ACETONE
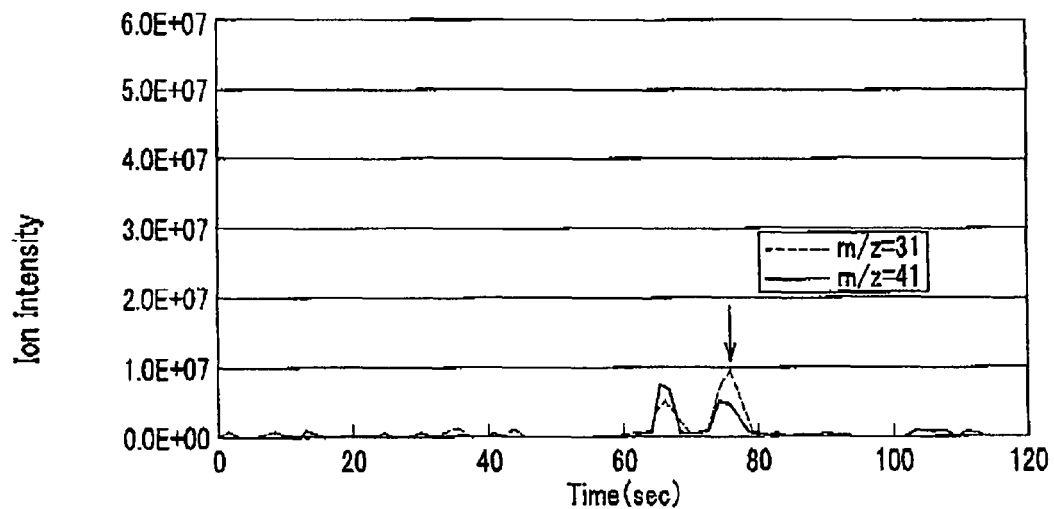
FIG.21C    SPECTRUM OF FRAGMENT IONS OF ACETONE
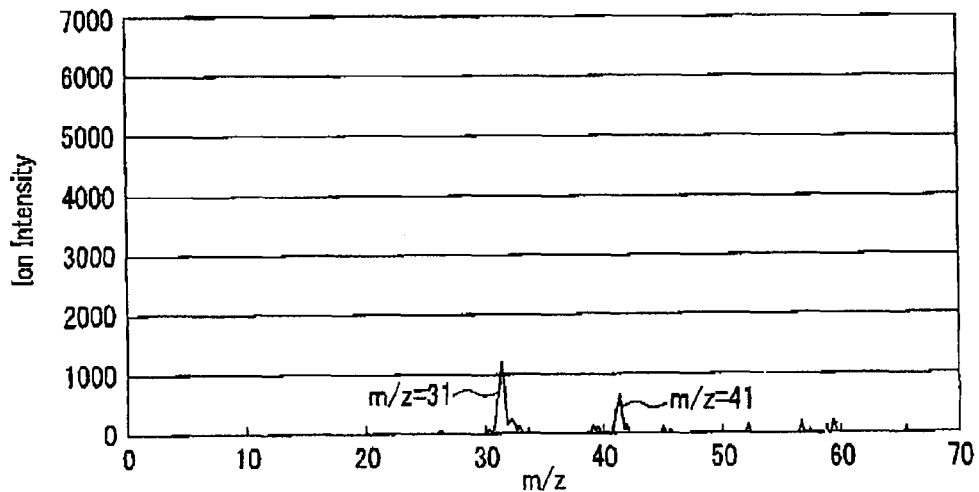

GAS COMPONENT COLLECTOR, GAS COMPONENT COLLECTING DEVICE, FILTER PRODUCING METHOD, AND GAS COMPONENT ANALYZING APPARATUS

CROSS REFERENCE TO RELATED APPLICATIONS

The present application claims priority from Japanese Patent Application No. 2006-285645 filed on Oct. 20, 2006, the content of which is hereby incorporated by reference into this application.

BACKGROUND OF THE INVENTION

1. Field of the Invention

The present invention relates to technology for a gas component collector, a gas component collecting device, a filter producing method, and a gas component analyzing apparatus and method that analyzes trace components in gas.

2. Description of the Related Art

The gas components of exhalation include trace metabolites produced inside the body of the person under test, and it is known that the concentrations of the trace metabolites or metabolic products themselves change depending on whether or not the person has a disease. Fundamental studies are in progress so as to help with diagnosing diseases by collecting and analyzing trace metabolite components from exhalation.

As explained above, technology of collecting trace metabolites, an exhalation collecting device has been proposed which collects components of exhalation by a collecting section having a cylindrical vent pipe in which a drying tube filled with a desiccant and an adsorbing tube filled with an adsorbent for carbon dioxide are inserted (refer to, for example, Japanese Patent Application Laid-Open Publication No. H09-210875 (hereinafter called reference 1), claims 1 and 4). The vent pipe of the collecting section of this exhalation collecting device has caps attached to opposite ends thereof to keep the inside of the vent pipe airtight. As for collecting exhalation gas, it is preferable to introduce exhalation at as low speed as possible through the opening of the entrance cap, and in order to adjust the flow speed, air-flow resistance is controlled through the diameter of the vent pipe, the opening diameter of the exit cap, and the grain sizes and filling densities of the desiccant and adsorbent.

Furthermore, a simple method and device for collecting atmospheric material has been proposed where porous bodies of an open structure having an appropriate length are formed inside a bare pipe made of metal, fused silica, or the like so as to fill the inside and where gas in the atmosphere is introduced by diffusion into the porous bodies of an open structure (refer to, for example, Japanese Patent Application Laid-Open Publication No. 2002-328077 (hereinafter called reference 2), claim 1).

In the reference 1, there is no specific description of the length and diameter of the adsorbing tube to reduce pressure loss. If pressure loss in the collecting section is high, the burden on a person under test breathing out exhalation may be great.

In the reference 2, there is no specific description of the method of reducing pressure loss when applied to the collection from exhalation gas to have exhalation actively introduced thereto. Further, there is no specific description of air-tightness before and after sampling, i.e., contamination before and after sampling.

SUMMARY OF THE INVENTION

The present invention was made in view of this background and an object thereof is to prevent contamination when collecting and analyzing gas components to be analyzed.

In order to solve the above problem, the present invention was made. According to the present invention, there is provided a filter comprising an adsorbent and an adsorbent holding plate having a first face, a second face and a plurality of holes that art bored through from the first face to the second face and are filled with the adsorbent adsorbing at least one gas component to be analyzed, the filter for which both $(AL-V)^2/L^3 \geq 0.003$ mm$^3$ and $V/AL \geq 0.3$ apply, where V is a total volume of the adsorbent, A is a sum of opening areas of the holes, and L is an average length of the holes and a holding container that houses the filter, the holding container having a first face side and a second face side, on at least one of which a first opening portion for introducing gas and a second opening portion for allowing the introduced gas to be discharged are formed.

BRIEF DESCRIPTION OF THE DRAWINGS

For a more complete understanding of the present invention and the advantages thereof, reference is now made to the following description taken in conjunction with the accompanying drawings wherein:

FIG. 2A is a side sectional view of the filter assembly, and FIG. 2B is a plan view of the filter assembly as seen from above in the page;

FIG. 3A is an example where there is slops in the shape of the holding container, and FIG. 3B is an example where the holding container covers the filter assembly to a minimum degree;

FIG. 5 is a schematic diagram of a gas component collecting device having two gas component collectors according to the embodiment;

FIG. 6A is a schematic side sectional view of the filter assembly producing apparatus, and FIG. 6B is a view of the filter assembly in production as seen from above in the page;

FIG. 7 is a flow chart showing the procedure of producing the gas component collector;

FIG. 14 is a flow chart showing the process flow of gas component analysis using an inert gas according to the embodiment;

FIG. 15 is a schematic diagram of a gas component analyzing apparatus using a solvent according to the embodiment;

FIG. 16 is a schematic diagram of another example (1st) of a gas component analyzing apparatus using a solvent according to the embodiment;

FIG. 19 is a flow chart showing the process flow of gas component analysis using a solvent according to the embodiment;

FIGS. 20A, 20B and 20C illustrate the influence of contamination on a gas component analyzing apparatus as a comparative example, FIG. 20A is a schematic diagram showing the configuration of the gas component analyzing apparatus as a comparative example, FIG. 20B shows a mass chromatograph of fragment ions of acetone for the comparative example; and FIG. 20C shows a spectrum of fragment ions of acetone for the comparative example; and FIGS. 21A, 21B and 21C illustrate the influence of contamination on a gas component analyzing apparatus according to the embodiment, FIG. 21A is a schematic diagram showing the configuration of the gas component analyzing apparatus of the embodiment, FIG. 21B shows a mass chromatograph of fragment ions of acetone for the embodiment, and FIG. 21C shows a spectrum of fragment ions of acetone for the embodiment.

DETAILED DESCRIPTION OF THE INVENTION

The best mode for carrying out the invention (hereinafter called an embodiment) will be described in detail with reference to the drawings as needed.

<Gas Component Collector>

Figure 1:
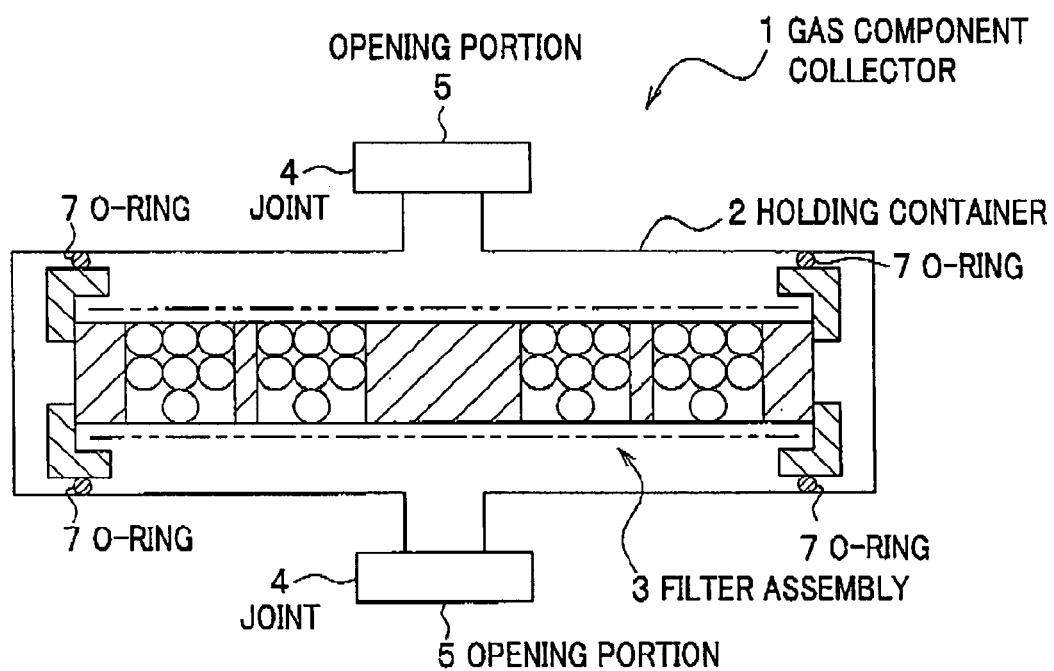
FIG. 1 is a schematic sectional view of a gas component collector according to an embodiment.

FIG. 1 is a schematic sectional view of a gas component collector according to the present embodiment.

A gas component collector 1 comprises a filter assembly (filter) 3, a holding container 2, and joints 4. The filter assembly 3 has a function to selectively collect gas components to be analyzed (hereinafter referred to as exhalation components, gas components, or to-be-measured components as needed) from gas (mainly exhalation) introduced in the gas component collector 1. The filter assembly 3 will be described later in detail with reference to FIG. 2. Because gas that is introduced into the gas component collector 1 is often exhalation, hereinafter the gas that is introduced is referred to as exhalation, and if another gas than that is introduced into the gas component collector 1, the other gas is referred to differently as needed.

The holding container 2 is a container having the filter assembly 3 housed therein and has two opening portions 5. The holding container 2 has a function to prevent the filter assembly 3 from being exposed to the atmosphere and collecting gas components from gas other than exhalation (contamination).

Figure 4:
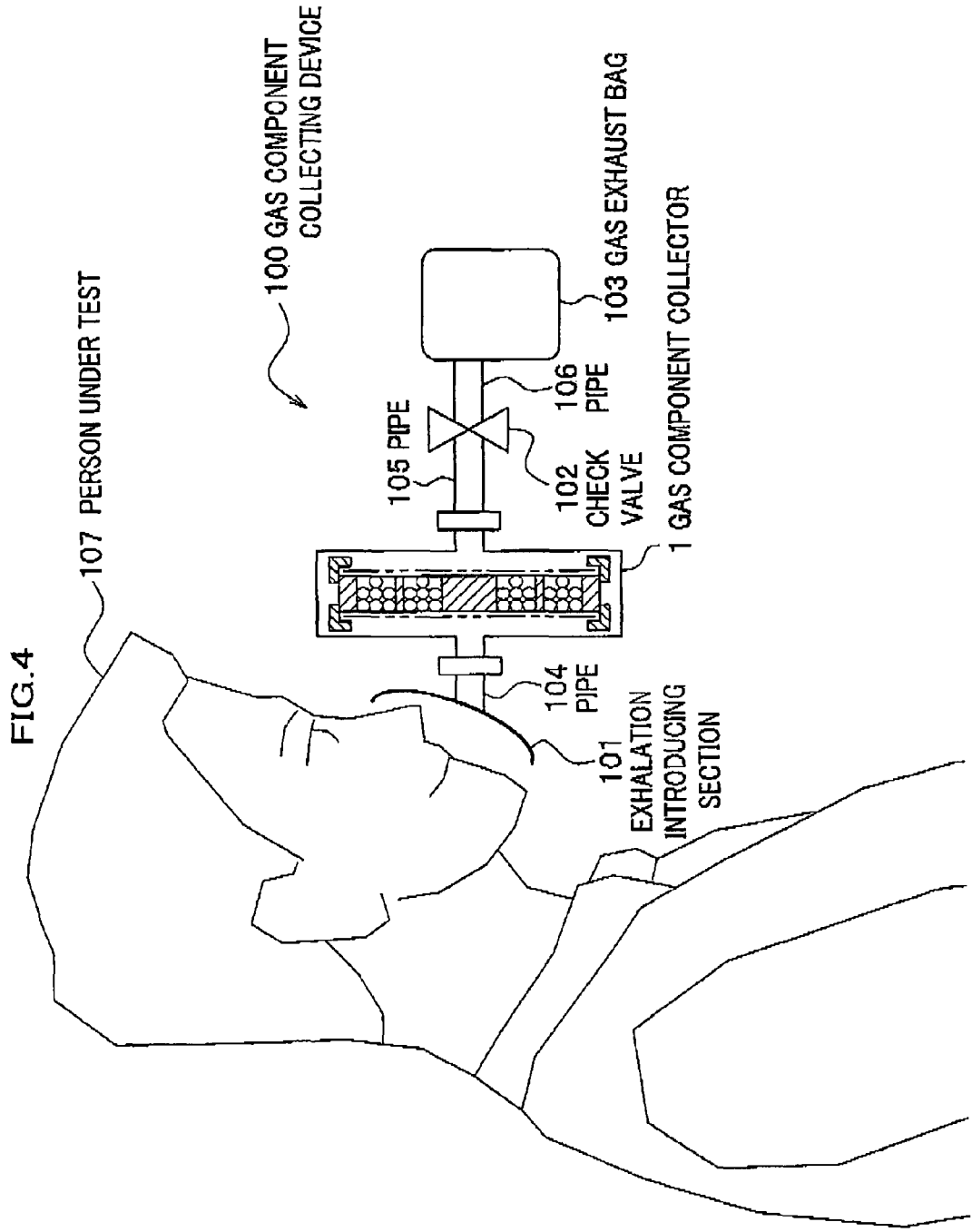
FIG. 4 is a schematic diagram of a gas component collecting device according to the embodiment.
Figure 9:
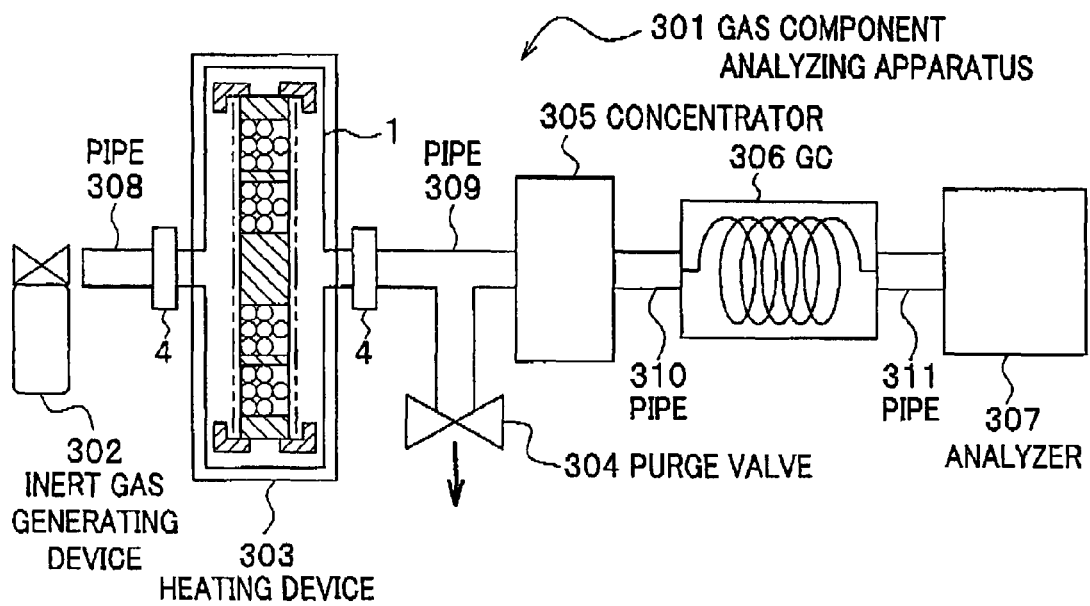
FIG. 9 is a schematic diagram of a gas component analyzing apparatus using an inert gas according to the embodiment.

The joints 4 are provided at the opening portions 5 of the holding container 2 and function to connect the gas component collector 1 to a gas component collecting device 100 of FIG. 4 or a gas component analyzing apparatus 301 of FIG. 9 when a pipe or the like is joined thereto. A plug (not shown) such as a cap can be attached to the joint 4, and by attaching this cap or the like, the opening portion 5 can be plugged when not in use. By plugging the opening portion 5 as such, the inside of the holding container 2 is put in an airtight state, and thus contamination can be prevented during movement or the like.

Furthermore, O-rings 7 may be provided as sealing means in between the filter assembly 3 and the holding container 2.

As such, if the filter assembly 3 is housed in the holding container 2 with sealing means such as the O-rings 7 sealing the periphery of the filter assembly 3 to the holding container 2 so that exhalation components do not escape around the periphery of the filter assembly 3, exhalation passes through holes 35 in an adsorbent holding plate 32 filled with au adsorbent, without leaking around the periphery of the filter assembly 3. Thus, the adsorption rate can be increased. The sealing means may be gaskets instead of the O-rings 7.

At least one place of the filter assembly 3 is preferably in contact with the inside of the holding container 2 via the O-ring 7 or the like. With such a configuration, when heating the filter assembly 3 together with the holding container 2 to separate exhalation components from an adsorbent 31 for analysis, the transmission of heat from the holding container 2 to the adsorbent 31 is improved. Considering heat transmission, sealing means is preferably made of metal.

Figure 2A:
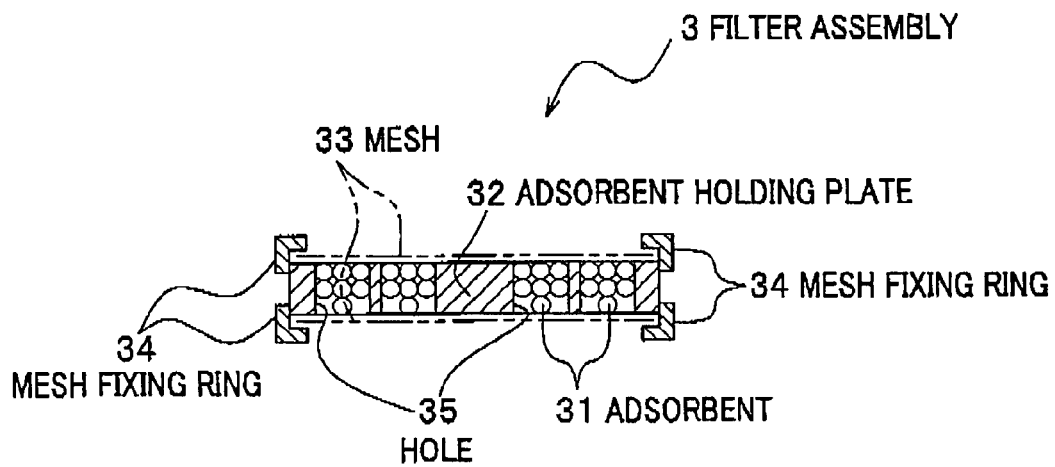
FIGS. 2A and 2B are views showing the configuration of a filter assembly according to the embodiment.
Figure 2B:
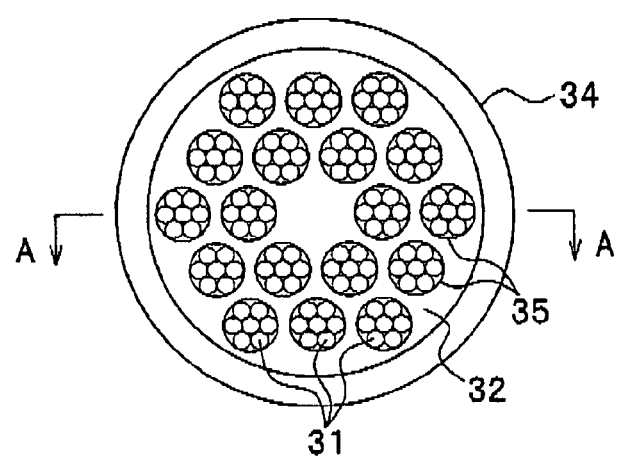

FIG. 2 is a view showing the configuration of the filter assembly according to this embodiment; FIG. 2A is a side sectional view of the filter assembly; and FIG. 2B is a plan view of the filter assembly as seen from above in the page. FIG. 2A is a sectional view along line A-A of FIG. 2B.

As shown in FIGS. 2A and 2B, the filter assembly 3 comprises the adsorbent holding plate 32 having a large number of holes 35, the adsorbent 31 filling the holes 35 in the adsorbent holding plate 32, meshes 33 provided on opposite faces of the adsorbent holding plate 32, and mesh fixing rings 34.

A plurality of the holes 35 are formed through the adsorbent holding plate 32 from its one face to the other face and filled with the granular adsorbent 31 as shown in FIGS. 2A and 2B. Further, the adsorbent holding plate 32 filled with the adsorbent 31 is sandwiched closely at its opposite faces by the meshes 33. The mesh 33 is fixed in predetermined position to the adsorbent holding plate 32 by the mesh fixing ring 34 fitting thereon.

The mesh fixing rings 34 are ring-like members that are secured to the periphery of the adsorbent holding plate 32 with use of screws or the like (not shown). As shown in FIG. 2A, the mesh fixing rings 34 are separate respectively on one face side and the other face side of the adsorbent holding plate 32 so as to fix the mesh 33 located on the one face side of the adsorbent holding plate 32 and the mesh 33 located on the other face side. The mesh size of the meshes 33 is set to be smaller than the grain size of the adsorbent 31. By this means, the adsorbent 31 can be prevented from fling out of the holes 35.

Although in the present embodiment the mesh fixing rings 34 are used to fix the meshes 33, the adsorbent holding plate 32 and the meshes 33 may be joined by spot welding or crimping.

Materials of members such as the meshes 33, the adsorbent holding plate 32, and the O-rings 7 are preferably, for example, metal such as stainless steel, which does not generate gas when heated. The material for the adsorbent 31 can be selected depending on the components to be measured but TENAX TA (registered trademark) or TENAX GR (registered trademark) of Buchem BV Company is usually used.

A material having antigen-antibody reaction may be used for the adsorbent 31. In this case, the holes 35 of the adsorbent holding plate 32 are filled with an antibody that shows antigen-antibody reaction to exhalation components to be detected, or the surfaces and the like of the adsorbent holding plate 32 are coated with the antibody. When exhalation is introduced into the gas component collector 1 having the filter assembly 3 of such a configuration, the adsorbent 31 adsorb exhalation components. Thereafter, the exhalation components are analyzed according to, e.g., a method that detects fluorescence. To be specific, the analysis is performed, e.g., as follows. First, the holes 35 of the adsorbent holding plate 32 are filled with antibody molecules (referred to as antibody molecules A) that show antigen-antibody reaction to exhalation components to be detected, or the surfaces or the like are coated with the antibody. When the gas component collector 1 having the filter assembly 3 collects from exhalation, the exhalation components are bound to the antibody molecules. Next, antibody molecules of the same type as the above antibody molecules that have a fluorochrome bound thereto (referred to as antibody molecules B) are prepared. Then, when the antibody molecules B are sprayed over the adsorbent 31 of the filter assembly 3 trapping the exhalation components, the antibody molecules B bind to the exhalation components bound to the antibody molecules A. Then, by measuring the fluorescence reaction of the antibody molecules B, the exhalation components of interest are detected.

In the present embodiment, a side close to a person under test 107 (see FIG. 4) is described as an upstream side, and a side far from the person under test 107 is described as a downstream side. Assuming that the pressure downstream of the filter assembly 3 is at the atmospheric pressure, the pressure upstream of the filter assembly 3 is positive by pressure loss when exhalation passes through the filter assembly 3, which becomes a resistance to the person under test 107 breathing out exhalation. That is, the lower the pressure loss is, the lower the pressure upstream of the filter assembly 3 is. Thus, the person under test 107 can breathe out exhalation easier.

Next a relationship between the amount of gas flowing through the filter assembly 3 and pressure loss due to that will be described.

Let A be the sum of the opening areas of the holes 35 (hereinafter referred to as an opening area), L be the average length of the holes 35, and V be the total volume of the adsorbent 31 filling the holes 35, then the volume of the portions through which exhalation can pass in the filter assembly 3 is expressed as AL−V. Thus, the apparent opening area through which exhalation can pass is expressed as follows:

$$(AL-V)/L. \tag{1}$$

The pressure loss P between upstream and downstream of the filter assembly 3 is expressed as follows:

$$P=Q/C, \tag{2}$$

where Q is the amount of exhalation and C is a conductance.

Assuming that the conductance C is that of a circular tube (for air at 20° C.), the conductance C is given by:

$$C=\{1349 \times d^4/L\} \times \{(P_1+P_2)/2\} [m^3/S], \tag{3}$$

where d is the apparent inner diameter of the circular tube=$2 \times ((AL-V)/\pi L)^{1/2}$, $P_1$ is the pressure upstream of the filter assembly 3, and $P_2$ is the pressure downstream of the filter assembly 3.

By using the above equations, the pressure loss P can be calculated from the total volume V of the adsorbent 31, the amount of exhalation Q, etc. The maximum amount of exhalation in usual exhalation is about 4 [l/min], and from the results of experiment by the inventors, it was found that for that amount or less, if the pressure loss P between upstream and downstream of the filter assembly 3 is at or below 10 [kPa]:

$$P=Q/C \leq 10 \times 10^3, \tag{4}$$

the person under test 107 does not feel a burden.

That is, substituting $P_1=110 \times 10^3$ [Pa], $P_2=100 \times 10^3$ [Pa], and $Q=4 \times 10^{-3} \times 10^5/60$ [Pa·m³/S] into the equations (3) and (4) and then substituting the equation (3) into the equation (4), the following is obtained:

$$(AL-V)^2/L^3 \geq 2.9 \times 10^{-12} [m^3] = 2.9 \times 10^{-3} [mm^3].$$

When it is satisfied that $(AL-V)^2/L^3 \geq 0.003$ [mm³], even if the person under test 107 breathes out at the exhalation amount of 4 [l/min], the pressure loss is at or below 10 [kPa], and thus the person under test 107 will not feel a burden.

Meanwhile, from the viewpoint of the analysis of exhalation gas, it is preferable that as much of the exhalation components as possible contacts the adsorbent 31 and is adsorbed by it. That is, if the ratio of the V to the AL (the volume ratio of the adsorbent 31 in the filter assembly 3), V/AL, is too small, most of the exhalation components does not contact the adsorbent 31 and exits the system. Thus, the concentrations of the components become small for the analysis after the heating of the adsorbent 31, and thus, highly sensitive measurement is not possible. According to the results of experiment by the inventors, if V/AL is equal to or more than 80%, the adsorption rate of the exhalation components is equal to or more than 90%; if at 30%, the adsorption rate is about 50%; and if it is 10%, the adsorption ae is as low as about 10%. Hence, it is desirable that V/AL $\geq$ 30%.

As the grain size of the adsorbent 31 becomes smaller, the total surface area becomes larger with the same amount of the adsorbent 31, thus increasing the capability of adsorbing gas components, but the volume ratio of the adsorbent 31 in the filter assembly 3 also increases, thus increasing the pressure loss. Accordingly, with the same grain size, by making the surface indented to increase the surface area, an adsorbing effect can be increased without the increase in the pressure loss. The adsorbent holding plate 32 is sandwiched in between a couple of meshes 33 of which mesh size is smaller than the gram size of the adsorbent 31.

With an example of the filter assembly 3 shown in FIG. 2 where the diameter of the hole 35 of the adsorbent holding plate 32 is $3 \times 10^{-3}$ [m], the average length of the hole 35 is $4 \times 10^{-3}$ [m], the number of the holes 35 is 18, the mesh size of the mesh 33 is 60, the adsorbent 31 is TENAX TA (registered trademark; mesh size=20/35) of Buchem BV Company, and where the volume of one grain of the adsorbent 31 is $308 \times 10^{-9}$ [m³], the total opening area of the holes 35 without the adsorbent 31 of the adsorbent holding plate 32 is $127 \times 10^{-6}$ [m²], and thus, the total volume of the holes 35 is $127 \times 10^{-6} \times 4 \times 10^{-3} = 509 \times 10^{-9}$ [m³]. Therefore, the volume ratio of the adsorbent 31 in the filter assembly 3 becomes 60%. Further, because $(AL-V)^2/L^3 = (509 \times 10^{-9} - 308 \times 10^{-9})^2/(4 \times 10^{-3})^3 = 630 \times 10^{-9}$ [m³] = 630 [mm³]), both $(AL-V)^2/L^3 \geq 0.003$ mm³ and V/AL $\geq$ 0.3 (30%) are satisfied.

The pressure loss when making gas flow through the filter assembly 3 at a flow velocity of 4 L/min was at about 1 kPa from the results of experiment, which is sufficiently smaller than 10 kPa at which the person under test 107 feels a resistance.

Further, a retrieval rate when using heptane as a standard sample was 50 to 70%, which was sufficient for analysis.

If the same amount of the adsorbent 31 is used, the flow velocity of gas passing through the filter assembly 3 needs to be reduced in order to reduce the pressure loss. Accordingly, to enlarge the total opening area A is effective, but if the adsorbent 31 is sandwiched in between the meshes 33 without the adsorbent holding plate 32 shown in FIG. 2 (to increase the total opening area A to the maximum), when moving the filter assembly 3, the grains of the adsorbent 31 will move and distributed so disproportionately that more grains are on one side than on the other. Thus, hardly contacting the adsorbent 31, exhalation gas exits the system when collecting exhalation components. As such, the adsorbent holding plate 32 has an effect of suppressing the uneven distribution of the adsorbent 31.

Figure 3A:
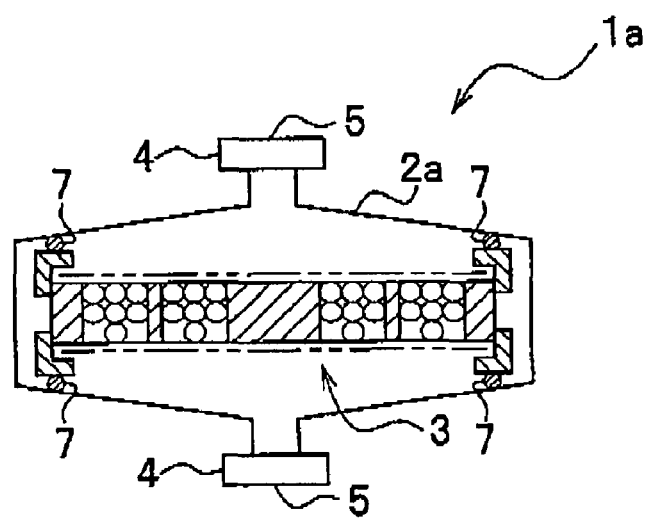
FIGS. 3A and 3B show other examples of the gas component collector according to the embodiment.
Figure 3B:
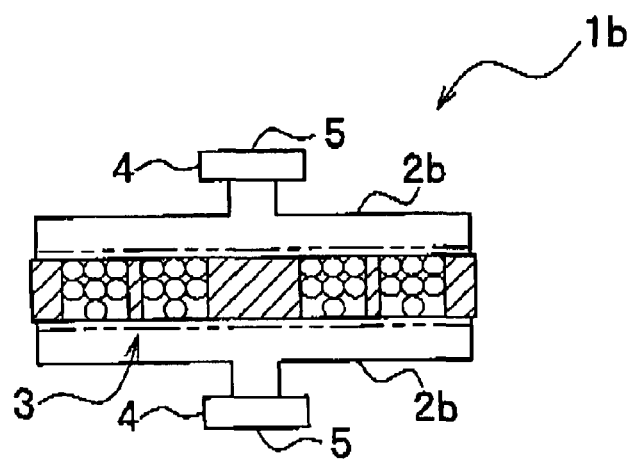

FIG. 3 shows other examples of the gas component collector according to the present embodiment; FIG. 3A is an example where there is a slope formed on the shape of the holding container; and FIG. 3B is an example where the holding container covers the filter assembly to a minimum degree.

In the example of FIG. 3A, a holding container 2a of a gas component collector 1a is shaped to have slopes extending from the opening portion 5 that become closer to the filter assembly 3. With the holding container in such a shape, exhalation introduced through one opening portion 5 proceeds along the slope, thus reducing a burden on the person under test 107.

In a gas component collector 1b of the example shown in FIG. 3B, while opposite ends of the filter assembly 3 are disposed outside a holding container 2b, all the adsorbent 31 (in the holes 35) is covered by the holding container 2b. The filter assembly 3 of FIG. 3B differs from the filter assembly 3 of FIG. 2 in that the mesh fixing rings 34 are not provided. In this case, the meshes 33 may be fixed by, for example, being sandwiched between the holding container 2b and the filter assembly 3. With the example of FIG. 3B, because exhalation does not escape around the periphery of the filter assembly 3, the O-rings 7 are not necessary.

As explained, as long as the holding container 2 is shaped such that at least the holes 35 filled with the adsorbent 31 are covered without exposing the adsorbent 31 to the outside air, the holding container 2 may have any shape.

The opening area of the opening portion 5 will be described below. As the opening area of the opening portion 5 becomes smaller, contamination from the atmosphere is reduced. Hence, usually the smaller opening area of the opening portion 5 is more preferable. To be more specific, the opening area of the opening portion 5 is preferably at least smaller than the total opening area of the holes 35 made in the adsorbent holding plate 32 (see FIG. 2).

<Gas Component Collecting Device>

Next, a gas component collecting device 100 using the gas component collector 1 of one of FIGS. 1 to 3 will be described with reference to FIGS. 4 and 5.

As to FIGS. 4 to 21, the O-rings 7 (see FIG. 1) are skipped from the figure.

FIG. 4 is a schematic diagram of the gas component collecting device according to the present embodiment.

The gas component collecting device 100 comprises an exhalation introducing section 101 (a gas introducing section), the gas component collector 1, a check valve 102, a exhaust gas bag 103 (a gas amount measuring section), and pipes 104 to 106 connecting them.

The exhalation introducing section 101 and the gas component collector 1 are connected via the pipe 104. The gas component collector 1 and the check valve 102 are connected via the pipe 105. Further, the check valve 102 and the exhaust gas bag 103 are connected via the pipe 106.

The exhalation introducing section 101 is mounted on the mouth and its vicinity of the person under test 107, and has a function to send exhalation breathed out by the person under test 107 to the gas component collector 1 via the pipe 104. The exhalation introducing section 101 is preferably shaped like a mask to cover the mouth but may be in the form of a pipe which is held in the mouth to introduce exhalation.

The gas component collector 1 has a function to selectively collect exhalation components to be analyzed from the exhalation sent from the exhalation introducing section 101. Because the gas component collector 1 has been described above with reference to FIGS. 1 to 3, a detailed description thereof will be omitted.

The check valve 102 has a function to prevent exhalation breathed out by the person under test 107 from flowing backward.

The exhalation breathed out by the person under test 107 is collected in the exhaust gas bag 103. The exhaust gas bag 103 is preferably provided which is capacious enough to accommodate a requisite amount of exhalation for analysis, for example, having a capacity of 0.2 L when fully inflated. The person under test 107 continues breathing out exhalation until the exhaust gas bag 103 is fully inflated. By this means, the amount of exhalation that has passed through the filter assembly 3 of the gas component collector 1 can be confirmed. Because the amount of exhalation components adsorbed onto the adsorbent 31 (see FIG. 2) depends on the amount of exhalation that has passed through, it is important to confirm the amount of exhalation in order to make sampling conditions the same. In the present embodiment, the exhaust gas bag 103 is used to check the amount of exhalation, but not being limited to this, for example, an integrating flow-meter or a balloon-like article may be used with which the amount of exhalation that has passed through the filter assembly 3 can be checked.

As mentioned above, the opening portion 5 of the gas component collector 1 is shaped such that it can be plugged with a cap or the like. The gas component collector 1 containing the filter assembly 3 having exhalation components exhaust adsorbed therein is removed from the gas component collecting device 100, and opposite ends of the gas component collector 1 are capped and sealed if not immediately analyzed. By transferring the gas component collector 1 in a sealed state to an analyzing place, contamination from the atmosphere can be prevented.

Next, the procedure of collecting exhalation components with use of the gas component collecting device 100 will be described with reference to FIGS. 2 and 4.

The person under test 107 mounts the exhalation introducing section 101 on the mouth and breathes out exhalation. The adsorbent 31 of the gas component collector 1 adsorbs exhalation components, thereby collecting the exhalation components. The adsorbent 31 selectively adsorbs the exhalation components exclusive of the other components in the exhalation. Inert gas such as nitrogen is not adsorbed onto the adsorbent 31 and flows out downstream of the filter assembly 3.

Consider removing the plug from the holding container 2, connecting it to the gas component collecting device 100, and collecting exhalation. Here, suppose that the amount of exhalation components adsorbed onto the adsorbent 31 (the adsorbed amount) is at 1 ng. Then, removing the gas component collector 1 from the gas component collecting device 100 and capping opposite ends thereof, air is also enclosed in the holding container 2, and to-be-measured components present in the enclosed air are also adsorbed in the filter assembly 3.

Here, let the volume of the space inside the gas component collector 1 in a sealed state be at 1000 mm³ and the concentration of to-be-measured components present in the atmosphere be at about 1 mg/m³ from the result of measurement, then the amount of the to-be-measured components present in the air enclosed in the holding container 2 becomes $1 \times 10^{-3} \times 1000 \times (10^{-3})^3 = 1 \times 10^{-9} = 1$ ng and is at the same concentration level as the adsorbed amount of the to-be-measured components contained in exhalation. Thus it is difficult to accurately measure the concentration of the to-be-measured components in exhalation.

If the concentration of the to-be-measured components contained in the atmosphere were always constant, the concentration level of the to-be-measured components in the atmosphere could be inferred. Thus, by subtracting the adsorbed amount of the to-be-measured components calculated based on that concentration level from the adsorbed amount of the to-be-measured components actually adsorbed onto the adsorbent 31, the adsorbed amount of the exhalation components in exhalation could be obtained precisely. However, because the gas concentrations of the atmosphere usually vary and cannot be inferred, by setting such that the adsorbed amount of the to-be-measured components from the atmosphere is as small as possible compared with the adsorbed amount of the to-be-measured components (i.e., the exhalation components) from exhalation, the influence of the to-be-measured components from the atmosphere needs to be minimized.

Accordingly, let D be the volume of the space inside the holding container 2 in a sealed state, B be the amount of the exhalation components adsorbed onto the adsorbent 31 upon the collection of the exhalation components, and C be the concentration of the to-be-measured components contained in the atmosphere, then $B > C \times D$ is desirably satisfied.

FIG. 5 is a schematic diagram of the gas component collecting device having two gas component collectors according to the present embodiment.

In FIG. 5, the same or like elements as in FIG. 4 are denoted by the same reference numerals with description thereof being omitted.

While the gas component collecting device 100 in FIG. 4 is configured to have one gas component collector 1, the gas component collecting device 100a of FIG. 5 is configured to have two gas component collectors 1 (1A and 1B). The two gas component collectors 1A and 1B are housed in a container 108 to form a unit. The two gas component collectors 1A and 1R may not be housed in the container 108 but joined by, e.g., adhesive or the like to form a unit.

With such a configuration, a comparison experiment is easily performed.

For example, in the configuration of FIG. 5, while the gas component collector 1A is connected to the exhalation introducing section 101 and the exhaust gas bag 103, the gas component collector 1B is connected to nowhere.

When exhalation is collected with such a configuration, the exhalation passes through only the gas component collector 1A. The plugs (not shown) that have been plugged in the joints of the gas component collector 1B are kept removed for the same time period during the collection of the exhalation by the gas component collector 1A, and the adsorbent 31 inside the gas component collector 1B is exposed to the atmosphere.

Then, after the completion of the collection of exhalation, the gas component collector 1A is removed from the gas component collecting device 100a, ad the opening portions 5 (see FIG. 1) of the gas component collectors 1A and 1B are plugged Then, by transferring the gas component collectors 1A and 1B in a sealed-by-plug state to an analyzing place, the gas component collectors 1A and 1B will have a history of the same conditions.

If the container 108 has a structured to be openable and closable, the gas component collectors 1A and 1B are removed from the container 108 in the analyzing place and are each analyzed and compared. Thereby, the comparison experiment for the exhalation components can be performed easily.

A pump 203 may be connected via a pipe on the downstream side of the gas component collector 1B, and the pump 203 may be operated so that the amounts of gases passing through the gas component collectors 1A and 1B become the same.

With the type of device that uses a single gas component collector 1 as shown in FIG. 4, using two separate gas component collectors 1 where one gas component collector 1 is provided in the gas component collecting device 100 with the other gas component collector 1 being not provided in the gas component collecting device 100, the same effect as with the device in FIG. 5 can be obtained by performing the collection of exhalation in a similar manner to the one described with reference to FIG. 5.

<Method of Producing Gas Component Collector>

Next, the method of producing the gas component collector 1 according to the present embodiment will be described with reference to FIGS. 6 to 8.

Figure 6A:
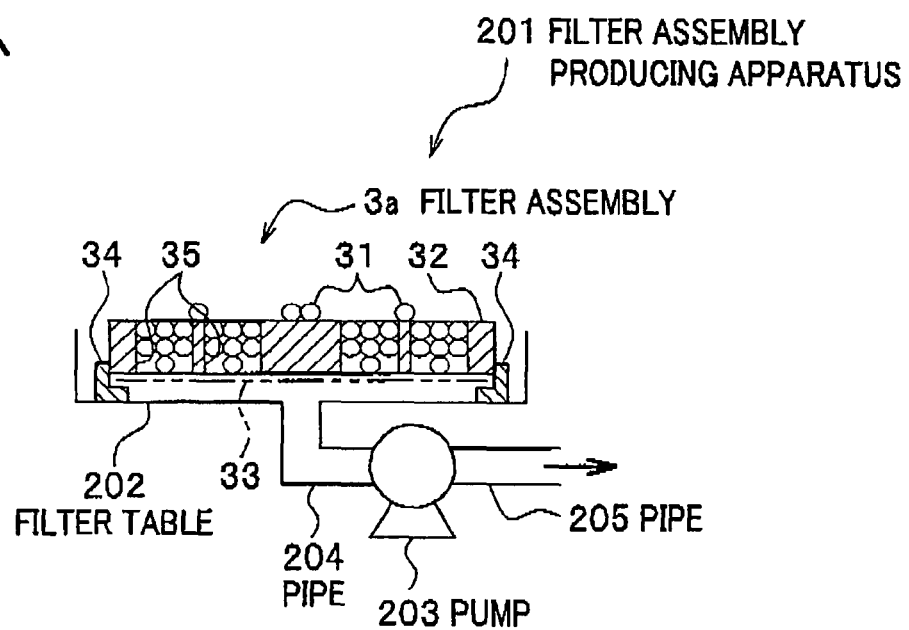
FIGS. 6A and 6B are schematic diagrams of a filter assembly producing apparatus according to the embodiment.
Figure 6B:
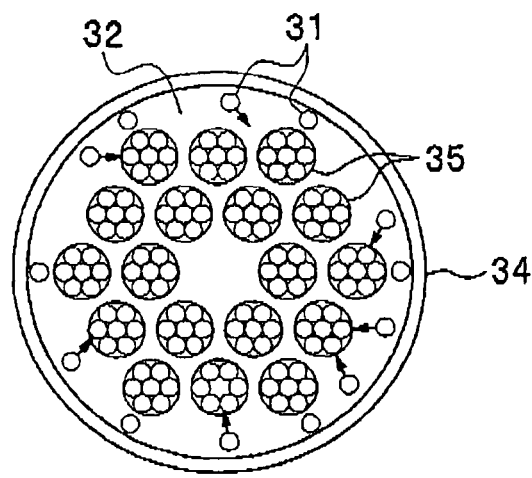
Figure 8:
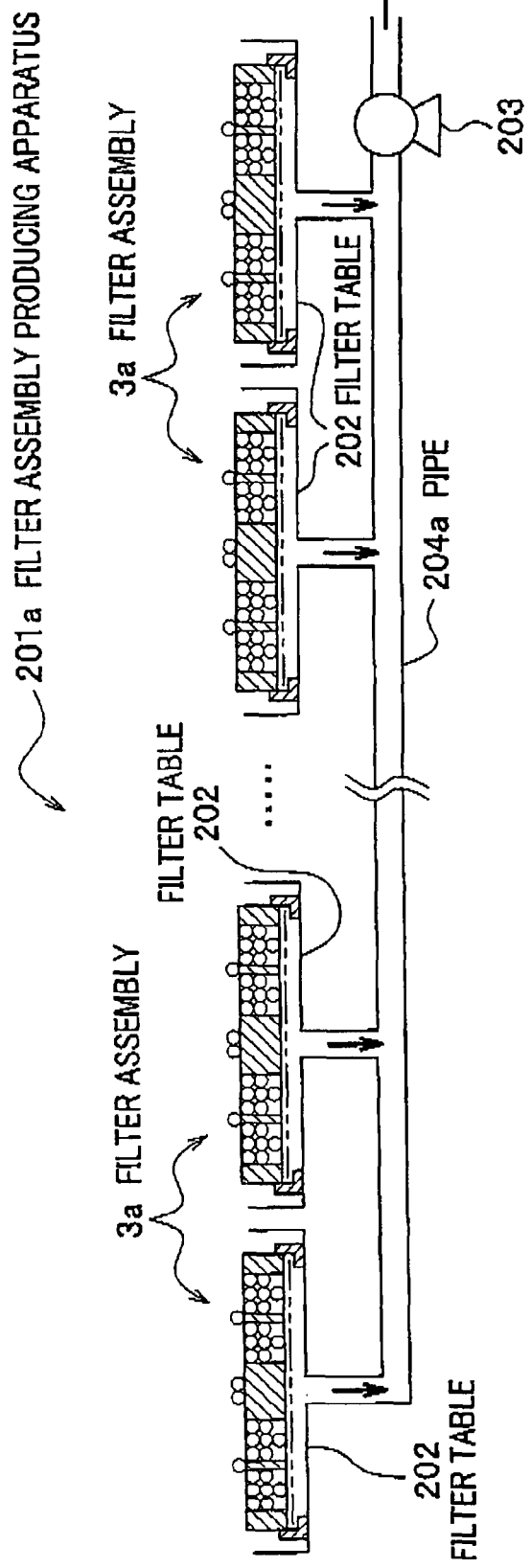
FIG. 8 is a schematic diagram of a filter assembly producing apparatus that produces a plurality of filter assemblies simultaneously.

The filter assembly 3a of FIGS. 6 to 8 differs from the filter assembly 3 of FIG. 2 in that the mesh 33 and mesh fixing ring 34 on one side are skipped FIG. 6 is a schematic diagram of a filter assembly producing apparatus according to the present embodiment; FIG. 6A is a schematic side sectional view of the filter assembly producing apparatus; and FIG. 6B is a view of the filter assembly in production as seen from above in the page.

As shown in FIG. 6A, the filter assembly producing apparatus 201 is configured to have a filter table 202, a pump 203, and pipes 204, 205.

The filter table 202 has a filter assembly 3a mounted thereon and has an opening in its middle portion to which the pipe 204 connecting to the pump 203 is connected. The filter table 202 and the pump 203 are connected by the pipe 204.

The pump 203 is connected to one end of the pipe 204 connecting to the filter table 202 and has a function to suck air above the filter table 202.

The pipe 205 is connected to the pump 203 and has a function to lead the air sucked out by the pump 203 to the outside.

The filter assembly 3a having a mesh 33 fixed to only one face thereof is mounted on the filter table 202 with the face having the mesh 33 fixed thereto underneath. The adsorbent holding plate 32 of the mounted filter assembly 3a is covered with grains of the adsorbent 31. When the pump 203 operates, air above the filter table 202 is sucked. At this time, as shown in FIG. 6B, air above the filter assembly 3a is sucked out through the holes 35 of the adsorbent holding plate 32.

Thereby, the adsorbent 31 on the adsorbent holding plate 32 is drawn into the holes 35. Because the mesh 33 is installed on the lower ends of the holes 35, grains of the adsorbent 31 drawn in do not reach the filter table 202 but fill the holes 35. The grains of the adsorbent 31 which could not enter the holes 35 are removed with a plate-like adsorbent removing tool (not shown).

Next, the procedure of producing the gas component collector 1 will be described in detail using FIG. 7 with reference to FIG. 6.

FIG. 7 is a flow chart showing the procedure of producing the gas component collector.

First, the mesh 33 is fixed to the adsorbent holding plate 32 at one face by the mesh fixing ring 34 (S101).

Next, the filter assembly 3a on whose one face there is a mesh 33 fixed is mounted on the filter table 202 with the mesh 33 placed underneath (S102), and the adsorbent holding plate 32 is covered with the adsorbent 31 (S103).

Then, by operating the pump 203, the adsorbent 31 fills the holes 35 of the adsorbent holding plate 32 (S104). If the adsorbent 31 fills the holes 35 to the same level, or higher, as the upper face of the adsorbent holding plate 32, the upper side of the adsorbent holding plate 32 is leveled with a plate-like adsorbent removing tool, and thereby the excess grains of the adsorbent 31 left outside the holes 35 or not fully contained in the holes 35 are removed (S105).

Thereafter, a mesh 33 is mounted on the face of the adsorbent holding plate 32 to which a mesh 33 has not been fixed, and the mesh 33 is fixed by the mesh fixing ring 34 (S106). Tis completes the filter assembly 3a.

Next, the holding container 2 is provided with the O-rings 7 (see FIG. 1) (S107).

Then, the filter assembly 3a is housed in the holding container 2, and the filter assembly 3a and the O-rings 7 of the holding container 2 (see FIG. 1) are fixed to each other by screws (not shown) (S108). This completes the gas component collector 1.

Conventionally, when filling with the adsorbent 31 is done, grains of the adsorbent 31 are put into the holes 35 one by one with use of a pair of tweezers or the like, which takes a lot of work hours. Further, there is the problem that during the filling, grains of the adsorbent 31 are flipped by the tweezers to be dispersed.

In the present embodiment, the holes 35 are filled with the adsorbent 31 by the suction of the pump 203, which prevents the adsorbent 31 from being dispersed, thus enabling efficient filling. The work conducted for comparison by the inventors showed that while work time required for filling with the adsorbent 31 according to the conventional method was about 60 minutes per plate, work time required for filling with the adsorbent 31 according to the present embodiment is about 5 minutes per plate, thus accomplishing a great improvement.

In the present embodiment, as shown in FIG. 6A, by covering the filter assembly 3a mounted on the filter table 202 with the adsorbent 31 and then the pump 203 sucking air downward from above the filter assembly 3a, the holes 35 are filled with the adsorbent 31, but not being limited to this, the configuration of FIG. 6A may be turned upside down. That is, by the pump 203 sucking air upward from under the filter assembly 3a, the adsorbent 31 put under the filter assembly 3a may be drawn upward to fill the holes 35.

FIG. 8 is a schematic diagram of a filter assembly producing apparatus that produces a plurality of filter assemblies simultaneously.

In FIG. 8, the same or like elements as in FIG. 6 are denoted by the same reference numerals with description thereof being omitted.

In a filter assembly producing apparatus 201a of FIG. 8, a plurality of filter tables 202 are provided. Each filter table 202 is connected with a pipe 204a connecting to a pump 203. With such a configuration, by operating the pump 203, air above the plurality of filter tables 202 is sucked out, and thus, filling with the adsorbent 31 can be performed simultaneously for the filter assembly 3a mounted on each filter table 202. Because the procedure of producing the filter assembly 3a on each filter table 202 and placing the produced filter assembly 3a into the holding container 2 to produce the gas component collector 1 is the same as for FIG. 7, detailed description is omitted <Gas Component Analyzing Apparatus Using Inert Gas>

Next, gas component analyzing apparatuses 301, 401 and gas component analyzing methods will be described with reference to FIGS. 9 to 19. In the present embodiment, gas chromatography is abbreviated to GC; high performance liquid chromatography to HPLC; a mass spectrometer to MS; and a combined device of gas chromatography and a mass spectrometer to GC/MS.

FIGS. 9 to 14 illustrate the gas component analyzing apparatus 301 and the gas component analyzing method, which use an inert gas in extracting exhalation components. FIGS. 15 to 19 illustrate the gas component analyzing apparatus 401 and the gas component analyzing method, which use a solvent for extracting exhalation components.

In FIGS. 9 to 14, the same or like elements as in FIGS. 1 and 2 are denoted by the same reference numerals with description thereof being omitted.

FIG. 9 is a schematic diagram of a gas component analyzing apparatus using an inert gas according to the present embodiment.

The gas component analyzing apparatus 301 comprises an inert gas generating device 302 (a carrier gas introducing section), a heating device 303 (a heater), the gas component collector 1, a purge valve 304, a concentrator 305, GC 306 (a component separator), an analyzer 307, and pipes 308 to 311 connecting them.

The inert gas generating device 302 has a function to generate an inert gas for expelling air from the pipes 308, 309 and the gas component collector 1 and sending exhalation components desorbed from the adsorbent 31 to the concentrator 305. The inert gas generated by the inert gas generating device 302 is sent to the gas component collector 1 via the pipe 308.

The heating device 303 houses the gas component collector 1 and has a function to heat the filter assembly 3 together with the gas component collector 1 (see FIG. 1). The heating device 303 is embodied by, for example, an electric heater or an infrared heater. The heating device 303 heats the adsorbent 31 together with the gas component collector 1, and gas containing desorbed exhalation components is transferred to the concentrator 305 by using as a carrier gas the inert gas generated by the inert gas generating device 302 such as helium gas.

The purge valve 304 has a function to discharge air from the gas component collector 1 and the pipe 309 to the outside with use of the inert gas.

The concentrator 305 has a function to concentrate again the exhalation components transferred thereto and perform rapid heating desorption, thereby improving the resolution of analysis by the analyzer 307. The concentrator 305 may use, for example, a cold trap where a fine capillary column is cooled by a Peltier device or liquid nitrogen so that components are adsorbed.

The GC 306 has a function to separate each component of the exhalation components.

The analyzer 307 measures the amount of each component separated by the GC 306. The analyzer 307 may be embodied by ion mobility, a mass spectrometer (MS), an electron capture detector (ECD), a flame ionization detector (FID), or the like, but not being limited to these, any analyzer which can analyze components may be used.

<Other Examples of Gas Component Analyzing Apparatus Using Inert Gas>

Next, other examples of the gas component analyzing apparatus 301 shown in FIG. 9 will be described using FIGS. 10 to 13 with reference to FIG. 9.

FIGS. 10 to 13 are schematic diagrams showing other examples of the gas component analyzing apparatus using an inert gas according to the present embodiment. In FIGS. 10 to 13, the same or like elements as in FIG. 9 are denoted by the same reference numerals with description thereof being omitted.

Figure 10:
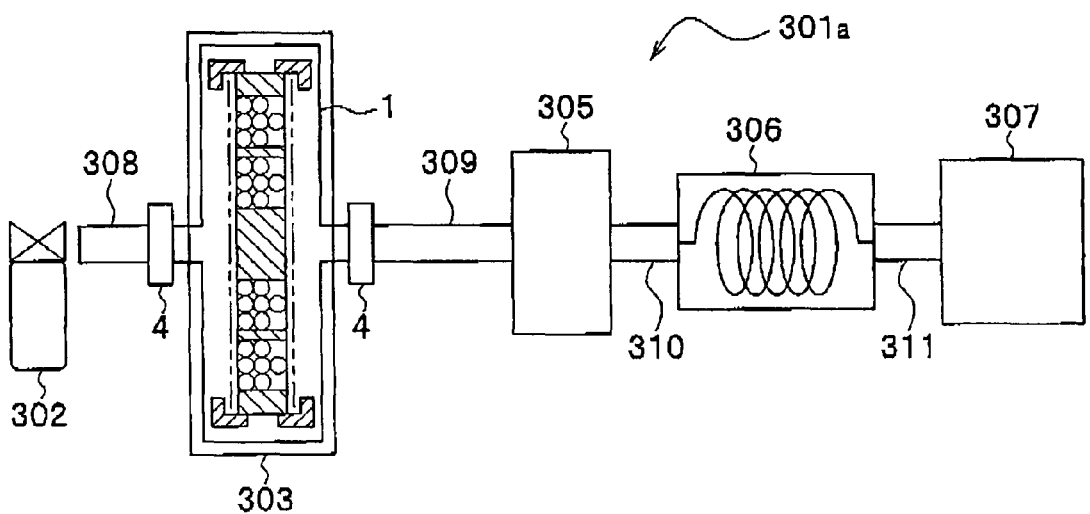
FIG. 10 is a schematic diagram of another example (1st) of a gas component analyzing apparatus using an inert gas according to the embodiment.

The purge valve 304 purges air that has diffused into the gas component collector 1 and the pipe 309 to the outside with use of an inert gas. During prig, the heating device 303 is kept from heating. If the filter assembly 3 is kept at a low temperature without being heated, the loss of exhalation components due to the purge is reduced because the exhalation components are not desorbed. If the air having diffused into the gas component collector 1 and the pipe 309 is not a problem for analysis, a gas component analyzing apparatus 301*a* as shown in FIG. 10 need not use the purge valve 304.

Figure 11:
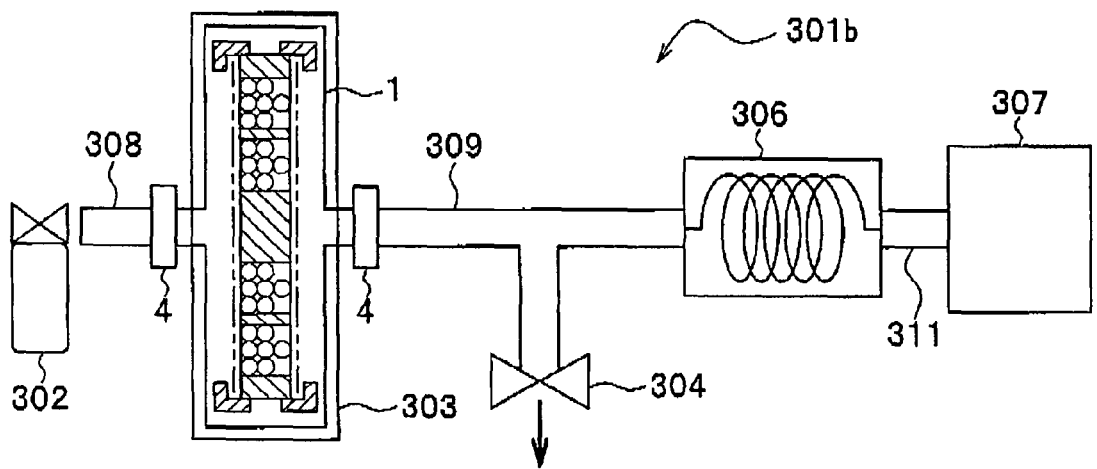
FIG. 11 is a schematic diagram of another example (2nd) of a gas component analyzing apparatus using an inert gas according to the embodiment.

Although the concentrator 305 performs the concentration and desorption of gas, thereby improving the resolution of the GC 306, if sufficiently high resolution is already obtained, a gas component analyzing apparatus 301*b* as shown in FIG. 11 need not use the concentrator 305.

Figure 12:
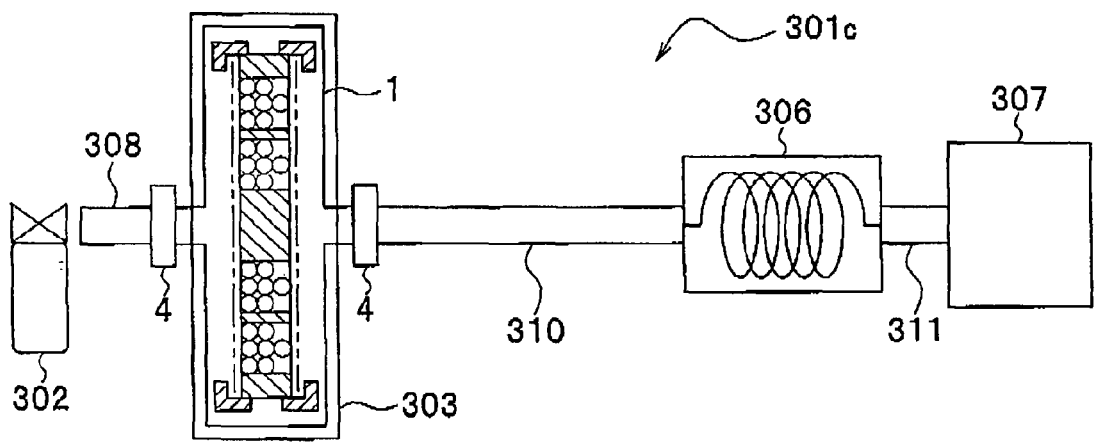
FIG. 12 is a schematic diagram of another example (3rd) of a gas component analyzing apparatus using an inert gas according to the embodiment.

If the air having diffused into the gas component collector 1 and the pipe 309 and the resolution are not a problem, a gas component analyzing apparatus 301*c* as shown in FIG. 12 may be configured without the purge valve 304 and the concentrator 305.

Figure 13:
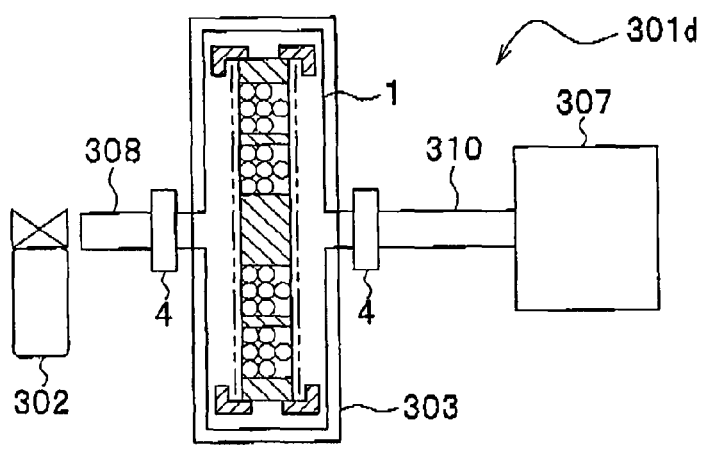
FIG. 13 is a schematic diagram of another example (4th) of a gas component analyzing apparatus using an inert gas according to the embodiment.

Further, if gas containing exhalation components need not be separated, a gas component analyzing apparatus 301*d* as shown in FIG. 13 may be configured without the GC 306. In FIG. 13, on the premise that air having diffused into the gas component collector 1 and the pipe 309 and the resolution are not a problem either, the purge valve 304 and the concentrator 305 are also skipped.

<Gas Component Analyzing Method Using Inert Gas>

Next, the gas component analyzing method using an inert gas according to the present embodiment will be described using FIG. 14 with reference to FIGS. 2, 4 and 9.

FIG. 14 is a flow chart showing the process flow of gas component analysis using an inert gas according to the present embodiment.

First, the gas component collector 1 is baked at a high temperature (S201) to make unknown gas components adsorbed onto the adsorbent 31 be desorbed beforehand.

Then, in an atmosphere of clean gas such as nitrogen or helium, the gas component collector 1 is cooled to a predetermined temperature (S202). Thereafter, the gas component collector 1 is set up in the gas component collecting device 100 (S203).

Then, exhalation components are collected according to the previously described method (S204). If exhalation components of high volatility are to be measured, the exhalation components can be efficiently adsorbed onto the surface of the adsorbent 31 by collecting exhalation components with both of the adsorbent 31 and the gas component collector 1 being cooled, which results in enabling analysis of good sensitivity. Conversely, if exhalation components of low volatility are to be measured by collecting with both of the adsorbent 31 and the gas component collector 1 being heated to a temperature which is not so high that the exhalation components are desorbed, impurity components of high volatility are not likely to be adsorbed onto the adsorbent 31. Thus the influence of the impurity components can be reduced. Exhalation is collected while measuring the amount of collected gas with use of the exhaust gas bag 103 (see FIG. 4 or 5), an integrating flow-meter, or the like. About 0.2 L is appropriate for the collected exhalation amount. The collected amount is adjusted depending on the sensitivity of the analyzer 307 used and the exhalation components of interest.

After exhalation is collected, the gas component collector 1 is removed from the gas component collecting device 100, and the gas component collector 1 is placed in the heating device 303 of the gas component analyzing apparatus 301 (S205). To be more specific, at the same time as the gas component collector 1 is removed from the gas component collecting device 100, the opening of each joint 4 is plugged with a cap or the like so as to put the inside of the gas component collector 1 in a sealed state. Then, the gas component collector 1 in this sealed state is transferred to the gas component analyzing apparatus 301, and immediately after the plugs are removed, the gas component collector 1 is placed in the heating device 303 of the gas component analyzing apparatus 301. As explained, setting up the gas component collector 1 in the heating device 303 can be achieved by a simple operation of merely removing the plugs from the gas component collector 1 and setting up. Thus, contamination can be prevented when being set up or during movement.

If the plugs of the gas component collector 1 are open for even a little time, air having flowed into the gas component collector 1 may diffuse into the pipe 309. Accordingly, at the same time as the inert gas generating device 302 generates inert gas, the purge valve 304 is opened. By this means, the inert gas is made to flow through the pipe 308, the gas component collector 1, and the pipe 309, thereby purging air having diffused into the pipes (S206). Where the purge valve 304 is not used (see FIGS. 10, 12, and 13), the process of step S206 can be omitted. After the purge finishes, the purge valve 304 is closed.

Then, the heating device 303 heats the filter assembly 3 together with the gas component collector 1, thereby making the exhalation components adsorbed onto the adsorbent 31 be desorbed (S207). For the heating, for example, an electric heater is used. The desorbed exhalation components are sent to the concentrator 305 via the pipe 309 by the inert gas generated by the inert gas generating device 302. In order to improve the resolution of analysis, the concentrator 305 uses, for example, a cold tap to make the exhalation components be adsorbed and concentrated again by an adsorbent in the concentrator 305 cooled to a low temperature and then perform rapid heating desorption (S208). Where the concentrator 305 is not used (see FIGS. 11, 12, and 13), the process of step S208 can be skipped.

The desorbed exhalation components are transferred to the GC 306 through the pipe 310, and each of the exhalation components is separated in the GC 306 (S209).

Each separated component is sent through the pipe 311 to the analyzer 307, which analyzes each of the sent components (S210). Where the GC 306 is not used (see FIG. 14), the process of step S209 can be omitted.

After the completion of measurement, the adsorbent 31 can be reused by heating it in an inert gas atmosphere to make the adsorbed components be completely desorbed (S211). In this case, for storage, opposite ends of the gas component collector 1 are plugged to seal the gas component collector 1, thereby preventing impurity components in the atmosphere from contaminating.

<Gas Component Analyzing Apparatus Using Solvent

FIG. 15 is a schematic diagram of a gas component analyzing apparatus using a solvent according to the present embodiment.

As shown in FIG. 15, a gas component analyzing apparatus 401 comprises an extracting section 402 that extracts the exhalation components adsorbed onto the adsorbent 31 (see FIG. 2) with use of a solvent and a component analyzing section 403 that analyzes the exhalation components exacted in the extracting section 402.

The extracting section 402 is configured to have the gas component collector 1 connected at its two joints 4 (see FIG. 1) to pipes 407 and 408 respectively. The pipe 407 is also referred to as a solvent introducing section.

The component analyzing section 403 comprises a solvent replacing portion 404, HPLC 405 (a component separator), an analyzer 406, and pipes 409 to 411 connecting them. The pipe 409 has a function to introduce the solvent having the exhalation components dissolved therein into the solvent replacing portion 404.

If the solvent used for the extraction is hardly ionized, the solvent replacing portion 404 has a function to replace the solvent with water or another solvent after vaporizing the solvent. Instead of the solvent replacing portion 404, a diluting portion having a function to dilute the solvent used for the extraction with water or another solvent may be used.

The HPLC 405 has a function to separate each of the exhalation components extracted in the solvent.

The analyzer 406 has the same function as the analyzer 307 of FIGS. 9 to 13.

Next, other examples of the gas component analyzing apparatus 401 of FIG. 15 will be described using FIGS. 16 to 18 with reference to FIG. 15.

Figure 17:
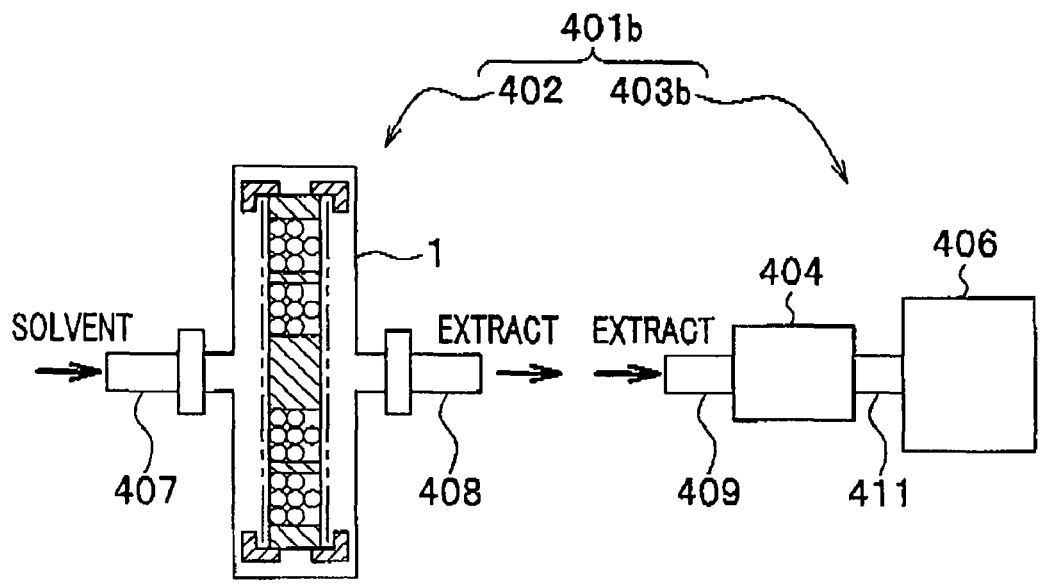
FIG. 17 is a schematic diagram of another example (2nd) of a gas component analyzing apparatus using a solvent according to the embodiment.
Figure 18:
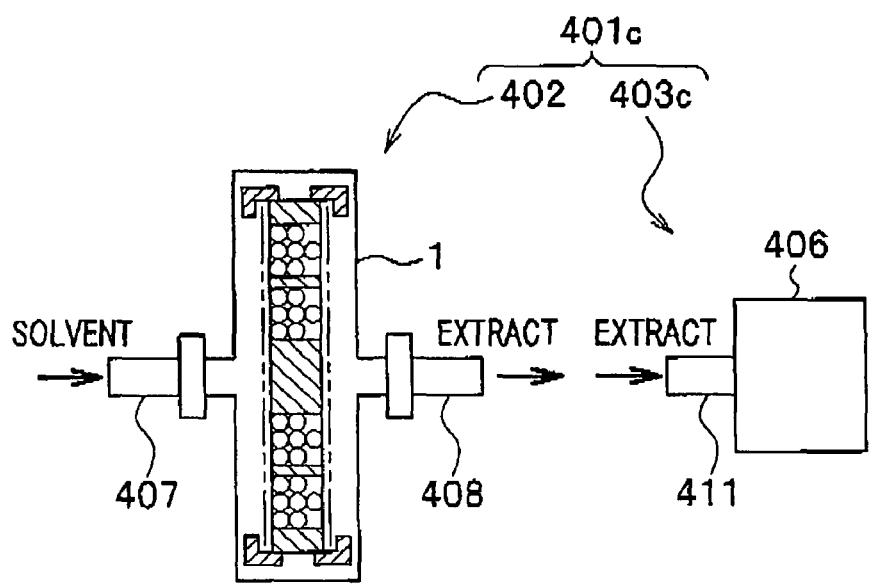
FIG. 18 is a schematic diagram of another example (3rd) of a gas component analyzing apparatus using a solvent according to the embodiment.

FIGS. 16 to 18 are schematic diagrams showing other examples of the gas component analyzing apparatus using a solvent according to the present embodiment. In FIGS. 16 to 18, the same or like elements as in FIG. 15 are denoted by the same reference numerals with description thereof being skipped.

If the solvent used in the extraction is easy to ionize without a need to replace or dilute the solvent with water or another solvent, a gas component analyzing apparatus 401a may be configured to have a component analyzing section 403a having the solvent replacing portion 404 or the diluting portion (not shown) omitted as shown in FIG. 16.

Further, if each of the exhalation components extracted in the solvent need not be separated, a gas component analyzing apparatus 401b may be configured to have a component analyzing section 403b having the HPLC 405 skipped as shown in FIG. 17.

If there is no need to replace or dilute the solvent with water or another solvent and to separate each of the exhalation components, a gas component analyzing apparatus 401c may be configured to have a component analyzing section 403c having the solvent replacing portion 404 or the diluting portion (not shown) and the HPLC 405 omitted as shown in FIG. 18.

Next, the gas component analyzing method using a solvent according to the present embodiment will be described using FIG. 19 with reference to FIGS. 2, 4 and 15.

FIG. 19 is a flow chart showing the process flow of gas component analysis using a solvent according to the present embodiment.

In FIG. 19, the same processes (S201 to S204) as in FIG. 14 are denoted by the same reference numerals with description thereof being omitted.

After exhalation is collected at the process of step S204, the gas component collector 1 is removed from the gas component collecting device 100 and set up in the exacting section 402 of the gas component analyzing apparatus 401 (S305). The method of removing and setting up the gas component collector 1 is the same as described in FIG. 14.

Next, the solvent is injected into the gas component collector 1 through the pipe 407, and the exhalation components are dissolved into the solvent thereby extracting the exhalation components (S306). Thereafter, the solvent containing the exited exhalation components (extract) is allowed to flow out through the pipe 408.

Once collected, preprocessing such as removing impurities through, e.g., filtering is performed on the extract (S307). If the preprocessing is not necessary, the process of step S307 can be skipped.

The preprocessed extract is introduced through the pipe 409 of the component analyzing section 403 into the solvent replacing portion 404. Then, if the solvent used in the extraction is hardly ionized, the solvent replacing portion 404 replaces the solvent of the extract with water or another solvent after vaporizing the solvent (a solvent replacing process) (S308). If the diluting portion (not shown) is used instead of the solvent replacing portion 404, the diluting portion dilutes the solvent of the extract with water or another solvent. If the solvent replacing portion 404 or the diluting portion (not shown) is not used (see FIGS. 16 and 18), the process of step S308 can be skipped.

The extract whose solvent is replaced at step S308 is transferred to the HPLC 405 through the pipe 410. Then, each of the exhalation components dissolved in the extract is separated in the HPLC 405 (S309). Each separated component is sent through the pipe 411 to the analyzer 406 and is analyzed by the analyzer 406 (S310). If the HPLC 405 is not used (see FIGS. 17 and 18), the process of step S309 can be skipped.

After the completion of measurement, the adsorbent 31 can be reused by heating it in an inert gas atmosphere to make the adsorbed components and solvent be completely desorbed (S311). In this case, for storage, opposite ends of the gas component collector 1 are plugged to seal the gas component collector 1, thereby preventing impurity components in the atmosphere from contaminating.

As explained, the gas component collector 1 can be easily set up in the gas component analyzing apparatuses 301, 301a to 301d (see FIGS. 9 to 13) or the gas component analyzing apparatuses 401, 401a to 401c (see FIGS. 15 to 18) because it is structured to be connected at the opening portions 5 (see FIG. 1) to them, and contamination can be prevented.

EXPERIMENTAL EXAMPLES

Next, the effect of the gas component collector 1 according to the present embodiment against contamination will be described with reference to FIGS. 20 and 21.

In FIGS. 20 and 21, the same or like elements as in FIG. 9 are denoted by the same reference numerals with description thereof being omitted.

FIG. 20 illustrates the influence of contamination on a gas component analyzing apparatus as a comparative example; FIG. 20A is a schematic diagram showing the configuration of the gas component analyzing apparatus as a comparative example; FIG. 20B shows a mass chromatograph of fragment ions of acetone for the comparative example; and FIG. 20C shows a spectrum of fragment ions of acetone for the comparative example.

FIG. 21 illustrates the influence of contamination on a gas component analyzing apparatus according to the present embodiment; FIG. 21A is a schematic diagram showing the configuration of the gas component analyzing apparatus of the embodiment; FIG. 21B shows a mass chromatograph of fragment ions of acetone for the embodiment; and FIG. 21C shows a spectrum of fragment ions of acetone for the embodiment.

The filter assembly 3 is taken out (i.e., exposed to the atmosphere) and then placed in a heating device 502 that uses lamp heating or the like of a gas component analyzing apparatus 501 of FIG. 20A. The subsequent analysis is the same as that of the present embodiment.

A gas component analyzing apparatus 301 of FIG. 21A is the same as the gas component analyzing apparatus 301 of FIG. 9.

The filter assembly 3 and the gas component collector 1 in FIGS. 20 and 21 were both heated in an inert gas atmosphere to make the substances adsorbed onto the adsorbent 31 be completely removed and then were provided in the heating devices 502, 303 respectively for background analysis. The substance for comparison was acetone that is contained in the atmosphere. Fragment ions (m/z=31) and (m/z=41) obtained after performing multiple mass spectrometry MS/MS) on ionized positive parent ions of acetone (m/z=59) were measured. Here, m/z denotes a mass-to-charge ratio (mass number (m) of an ion divided by its charge number (z)).

FIGS. 20C and 21C show spectrums at the times indicated by the downward arrows in FIGS. 203 and 21B. In FIGS. 20C and 21C, the peaks indicated by m/z=31 and m/z=41 indicate acetone. In FIGS. 20B and 21B, the ordinate represents ion intensity, and the abscissa represents time. In FIGS. 20C and 21C, the ordinate represents ion intensity, and the abscissa represents m/z.

By comparing the spectra in FIGS. 20C and 21C, it is found that the detected amount of acetone is smaller for FIG. 21C. Hence, it proves that with the gas component collector 1 according to the present embodiment, contamination by acetone is less in amount.

<Effect>

As shown in FIGS. 1 and 2, the holding container 2 is provided at least either on a first face side or a second face side of the filter assembly 3 with each of a first opening portion 5 for introducing gas and a second opening portion 5 for allowing the introduced gas to exit and is structured to house the filter assembly 3. By this means, the filter assembly 3 can be isolated from the atmosphere, thus preventing contamination of the filter assembly 3.

Further, letting V be the total volume of the adsorbent 31, A be the sum of the opening areas of the holes 35, and L be the average length of the holes 35, the filter assembly 3 has a structured to satisfy both $(AL-V)^2/L^3 \geqq 0.003$ mm$^3$ and $V/AL \geqq 0.3$. Thus, pressure loss when collecting gas components to be analyzed can be reduced, thereby reducing a burden on the person under test 107.

Yet further, with the two opening portions 5 being shaped to be plugged, the gas component collector 1 has such a structure that its inside is sealable. Thus, contamination can be prevented during movement or when being set up in the gas component analyzing apparatus 301.

Because sealing means can be placed in between the filter assembly 3 and the holding container 2, gas components to be analyzed can be prevented from leaking around the periphery of the filter assembly 3.

Because the gas component collector 1 has a structure to be connected at the opening portions 5, the gas component collector 1 can be easily set up in the gas component collecting device 100 (see FIG. 4) and the gas component analyzing apparatuses 301, 401 (see FIGS. 9 and 15), and also contamination can be prevented.

As shown in FIG. 6, the method of producing the filter assembly 3a comprises a step of covering the first face of the filter assembly 3a before filled with the adsorbent 31 with the mesh 33 finer than the grain size of the adsorbent 31; a step of mounting on the filter table 202 provided with the pump 203 to suck gas the filter assembly 3a with the first face covered by the mesh 33 being opposite the pump 203; a step of sucking gas by the pump 203 so as to draw the adsorbent 31 together with the gas, thereby filling the holes 35 with the adsorbent 31; a step of removing the excess grains of the adsorbent 31 from the second face; and a step of covering the second face with a mesh 33. Therefore, the adsorbent 31 is prevented from being dispersed, and work time is reduced.

Furthermore, as shown in FIG. 8, by mounting a plurality of filter assemblies 3a on a plurality of filter tables 202 and simultaneously sucking the adsorbent 31 by the pump 203, the plurality of filter assemblies 3a can be produced simultaneously.

There is provided a production method for producing a filter comprising an adsorbent holding plate and an adsorbent, the adsorbent holding plate having a first face, a second face and a plurality of holes that are bored through from the first face to the second face and are filled with an adsorbent adsorbing at least one gas component to be analyzed, comprising the steps of attaching a mesh whose mesh size is smaller than a grain size of the adsorbent to the first face of the adsorbent holding plate unfilled with the adsorbent, placing the adsorbent holding plate on a filter table provided with a sucking portion to suck air so that the first face covered with the mesh comes onto the sucking portion, filling the holes with the adsorbent that is sucked by sucking air, removing an extra part of the adsorbent over the second face and attaching another mesh onto the second face.

There is provided the method of producing filters according to the foregoing, wherein on the filter table are formed a plurality of sucking portions, on each of which the filter is placed and wherein a plurality of the filters are produced at one time.

A gas component analyzing apparatus which analyzes at least one gas component of interest, comprises a gas component collector that has collected the at least one gas component of interest; an analyzer that analyzes the at least one gas component of interest; and a solvent introducing section that introduces into the gas component collector a solvent to dissolve the at least one gas component of interest adsorbed in the gas component collector and send the dissolved at least one gas component to the analyzer. The gas component collector comprises a filter comprising an adsorbent and an adsorbent holding plate having a first face, a second face and a plurality of holes that are bored through from the first face to the second face and are filled with a macular adsorbent adsorbing at least one gas component of interest, the filter satisfying $(AL-V)^2/L^3 \geqq 0.003$ mm$^3$ and $V/AL \geqq 0.3$, where V is a total volume of the adsorbent, A is a sum of the opening areas of the holes, and L is an average length of the holes; and a holding container that houses the filter. The holding container has a first face side on which a first opening portion connected to the first pipe is formed and a second face side on which a second opening portion connected to the second pipe is formed. The holding container houses the filter that is provided on the first face side of the filter with a first opening portion for introducing gas and on the second face side with a second opening portion for allowing the introduced gas to exit. The gas component collector is attachable and detachable at the first opening portion and second opening portion to and from the gas component analyzing apparatus.

There is provided the gas component analyzing apparatus according to the foregoing, further comprising a solvent replacing portion that replaces the solvent having the at least one gas component dissolved therein with water or another solvent or a diluting portion that dilutes the solvent having the at least one gas component dissolved therein with water or another solvent in between the gas component collector and the analyzer.

There is provided the gas component analyzing apparatus according to the same, further comprising a component separator in between the gas component collector and the analyzer, the component separator separating each of the at least one gas component dissolved in the solvent.

There is provided the gas component analyzing apparatus according to the foregoing, wherein the component separator is of liquid chromatography.

There is provided a gas component analyzing method for a gas component analyzing apparatus comprising: a gas component collector that has collected at least one gas component of interest; a heater that heats the gas component collector, an analyzer that connects to the gas component collector and analyzes the at least one gas component of interest; and a carrier gas introducing section that introduces a carrier gas into the gas component collector to send the desorbed at least one gas component of interest from the gas component collector to the analyzer, wherein the gas component collector comprises a filter comprising an adsorbent and an adsorbent holding plate having a first face, a second face and a plurality of holes that are bored through from the first face to the second face and are filled with the adsorbent adsorbing the at least one gas component of interest, the filter satisfying $(AL-V)^2/L^3 \geqq 0.003$ mm$^3$ and $V/AL \geqq 0.3$, where V is the total volume of the adsorbent, A is the sum of the opening areas of the holes, and L is the average length of the holes; and a holding container housing the filter that is provided on the first face side of the filter with a first opening portion for introducing gas and on the second face side with a second opening portion for allowing the introduced gas to be discharged, wherein the gas component collector is detachably installed at the first opening portion and second opening portion in the gas component collecting device, the gas component analyzing method wherein the heater heats the gas component collector that has collected the at least one gas component; the carrier gas introduced through the carrier gas introducing section sends the at least one gas component desorbed by the beating from the adsorbent of the gas component collector to the analyzer, and the analyzer analyzes the at least one gas component sent.

There is provided the gas component analyzing method according to the foregoing, wherein the gas component analyzing apparatus fixer comprises a concentrator in between the gas component collector and the analyzer, the concentrator concentrating and heating the at least one gas component sent from the gas component collector.

There is provided the gas component analyzing method according to the same, wherein the gas component analyzing apparatus further comprises a purge section in between the gas component collector and the analyzer, and before the gas component collector is heated and after the carrier gas is introduced through the carrier gas introducing section, the purge section is opened.

There is provided the gas component analyzing method according to the same, wherein the gas component analyzing apparatus further comprises a component separator in between the gas component collector and the analyzer, the component separator separating each of the at least one gas component sent from the gas component collector and sending each said separated gas component to the analyzer, the analyzer analyzing each said separated gas component sent.

There is provided the gas component analyzing method according to the foregoing, wherein the component separator is of gas chromatography.

There is provided a gas component analyzing method for a gas component analyzing apparatus comprising a gas component collector that has collected the at least one gas component of interest; an analyzer that analyzes the at least one gas component of interest; and a solvent introducing section that introduces into the gas component collector a solvent to dissolve the at least one gas component of interest adsorbed in the gas component collector and send the dissolved at least one gas component to the analyzer, wherein the gas component collector comprises a filter comprising an adsorbent and an adsorbent holding plate having a first face, a second face and a plurality of holes that are bored through from the first face to the second face and are filled with the adsorbent adsorbing the at least one gas component of interest, the filter satisfying that $(AL-V)^2/L^3 \geqq 0.003$ mm$^3$ and $V/AL \geqq 0.3$, where V is the total volume of the adsorbent, A is the sum of the opening areas of the holes, and L is the average length of the holes; and a holding container housing the filter that is provided on the first face side of the filter with a first opening portion for introducing gas and on the second ace side with a second opening portion for allowing the introduced gas to exit, wherein the gas component collector is attachable and detachable at the first opening portion and second opening portion to and from the gas component analyzing apparatus, the gas component analyzing method wherein the solvent introduced through the solvent introducing section dissolves the at least one gas component adsorbed onto the adsorbent of the gas component collector; the solvent having the at least one gas component dissolved therein is sent to the analyzer; and the analyzer analyzes the at least one gas component dissolved in the solvent sent.

There is provided the gas component analyzing method according to the foregoing, wherein the gas component analyzing apparatus flier comprises a solvent replacing portion in between the gas component collector and the analyzer, the solvent replacing portion replacing the solvent having the at least one gas component dissolved therein with water or another solvent.

There is provided the gas component analyzing method according to the same, wherein the gas component analyzing apparatus further comprises a diluting portion in between the gas component collector and the analyzer, the diluting portion diluting the solvent having the at least one gas component dissolved therein with water or another solvent.

There is provided the gas component analyzing method according to the same, wherein the gas component analyzing apparatus further comprises a component separator in between the gas component collector and the analyzer, the component separator separating each of the at least one gas component sent from the gas component collector and sending each said separated gas component to the analyzer, the analyzer analyzing each said separated gas component sent.

There is provided the gas component analyzing method according to the foregoing, wherein the component separator is of liquid chromatography.

What is claimed is:

1. A gas component collector comprising:
   a filter comprising an adsorbent and an adsorbent holding plate having a first face, a second face and a plurality of holes that are formed by boring through from the first face to the second face and are filled with the adsorbent adsorbing at least one gas component to be analyzed, the filter for which both $(AL-V)^2/L^3 \geq 0.003$ mm$^3$ and V/AL $\geq 0.3$ apply, where V is a total volume of the adsorbent, A is a sum of opening areas of the holes, and L is an average length of the holes; and
   a holding container that houses the filter, the holding container having a first face side and a second face side, on at least one of which a first opening portion for introducing gas and a second opening portion for allowing the introduced gas to be discharged are formed.

2. The gas component collector according to claim 1, wherein the first opening portion and the second opening portion are shaped to he plugged, and thus the inside of the gas component collector is sealable.

3. The gas component collector according to claim 1, further comprising sealing means placed in between the filter and the holding container.

4. The gas component collector according to claim 3, wherein the sealing means comprises a seal ring made of metal.

5. The gas component collector according to claim 1, wherein an opening area of at least one of the first opening portion and the second opening portion is smaller than the sum of the opening areas of the openings.

6. The gas component collector according to claim 1, wherein B >C×D, where D is a volume of a space inside the holding container, B is an amount of the to-be-analyzed at least one gas component adsorbed onto the adsorbent, and C is a concentration of the to-be-analyzed at least one gas component contained in the atmosphere.

7. A gas component collecting device which collects at least one gas component to be analyzed, comprising:
   a gas introducing section that introduces gas, a gas component collector that selectively collects the to-be-analyzed at least one gas component contained in the gas,
   a first pipe that connects between the gas introducing section and the via a first pipe, and
   a second pipe that allows the introduced gas to be discharged out of the gas component collecting device,
   wherein the gas component collector comprises:
   a filter comprising an adsorbent and an adsorbent holding plate having a first face, a second face and a plurality of holes that are formed by boring through from the first face to the second face and are filled with the adsorbent adsorbing at least one gas component to be analyzed, the filter for which both $(AL-V)^2/L^3 \geq 0.003$ mm$^3$ and V/AL $\geq 0.3$ apply, where V is a total volume of the adsorbent, A is a sum of opening areas of the holes, and L is an average length of the holes; and
   a holding container housing the filter having a first face side on which a first opening portion connected to the first pipe is formed and a second face side on which a second opening portion connected to the second pipe is formed,
   wherein the gas component collector is detachably installed at the first opening portion and second opening portion in the gas component collecting device.

8. The gas component collecting device according to claim 7, wherein a gas amount measuring section to measure an amount of gas is connected to an end of the second pipe to which the gas component collector is not connected.

9. The gas component collecting device according to claim 8, wherein the gas amount measuring section is an integrating flow-meter.

10. The gas component collecting device according to claim 8, wherein the gas amount measuring section is a bag having a particular capacity.

11. The gas component collecting device according to claim 7, further comprising a valve installed in the second pipe to prevent the reverse flow of the gas.

12. The gas component collecting device according to claim 7,
    wherein the gas component collecting device comprises at least two of the gas component collectors.

13. The gas component collecting device according to claim 7, wherein B>C×D applies, where D is the volume of the space inside the holding container, B is the amount of the to-be-analyzed at least one gas component adsorbed onto the adsorbent, and C is the concentration of the to-be-analyzed at least one gas component contained in the atmosphere.

14. A gas component analyzing apparatus which analyzes at least one gas component of interest, comprising:
    a gas component collector that has collected the at least one gas component of interest;
    a heater that heats the gas component collector;
    an analyzer that connects to the gas component collector and analyzes the at least one gas component of interest; and
    a carrier gas introducing section that introduces into the gas component collector a carrier gas to send a desorbed at least one gas component of interest from the gas component collector to the analyzer,
    wherein the gas component collector comprises:
    a filter comprising an adsorbent and an adsorbent holding plate having a first face, a second face and a plurality of holes that are formed by boring through from the first face to the second face and are filled with the adsorbent adsorbing at least one gas component to be analyzed, the filter for which both $(AL-V)^2/L^3 \geq 0.003$ mm$^3$ and V/AL $\geq 0.3$ apply, where V is a total volume of the adsorbent, A is a sum of opening areas of the holes, and L is an average length of the holes; and
    a holding container that houses the filter, the holding container having a first face side and a second face side, on at least one of which a first opening portion for introducing gas and a second opening portion for allowing the introduced gas to be discharged are formed,
    wherein the gas component collector is detachably installed at the first opening portion and second opening portion in the gas component analyzing apparatus.

15. The gas component analyzing apparatus according to claim 14, further comprising a concentrator in between the gas component collector and the analyzer, the concentrator concentrating and heating the at least one gas component of interest sent from the gas component collector.

16. The gas component analyzing apparatus according to claim 14, further comprising a purge section in between the gas component collector and the analyzer.

17. The gas component analyzing apparatus according to claim 14, further comprising a component separator in between the gas component collector and the analyzer, the component separator separating each of the at least one gas component of interest sent from the gas component collector.

18. The gas component analyzing apparatus according to claim 17, wherein the component separator is of gas chromatography.

* * * * *

UNITED STATES PATENT AND TRADEMARK OFFICE
CERTIFICATE OF CORRECTION

| | | |
|---|---|---|
| PATENT NO. | : 7,882,754 B2 | Page 1 of 1 |
| APPLICATION NO. | : 11/907905 | |
| DATED | : February 8, 2011 | |
| INVENTOR(S) | : Suga et al. | |

It is certified that error appears in the above-identified patent and that said Letters Patent is hereby corrected as shown below:

On the Title Page of the patent, please add Item (30) Foreign Document Priority Data.,

-- JP2006-285645 (10/20/2006) --

Signed and Sealed this
Fourteenth Day of June, 2011

David J. Kappos
*Director of the United States Patent and Trademark Office*